United States Patent
Sato et al.

[11] Patent Number: 5,814,324
[45] Date of Patent: Sep. 29, 1998

[54] INJECTABLE COMPOSITION AND A METHOD OF PRODUCING THE SAME

[75] Inventors: Jun Sato, Kawanishi; Akiko Watanabe, Kobe; Susumu Iwasa, Tsuzuki-gun, all of Japan

[73] Assignee: Takeda Chemical Industries, Ltd., Osaka, Japan

[21] Appl. No.: 454,151

[22] PCT Filed: Feb. 23, 1995

[86] PCT No.: PCT/JP95/00260

§ 371 Date: Jun. 13, 1995

§ 102(e) Date: Jun. 13, 1995

[87] PCT Pub. No.: WO95/22973

PCT Pub. Date: Mar. 8, 1995

[30] Foreign Application Priority Data

Feb. 25, 1994 [JP] Japan ................................. 6-028474

[51] Int. Cl.⁶ .......................... A01N 25/04; A61K 31/41; B01J 13/00
[52] U.S. Cl. .......................... 424/405; 252/312; 252/314; 424/423; 514/383; 514/938
[58] Field of Search .............. 252/312; 514/383, 514/938; 424/405, 423

[56] References Cited

U.S. PATENT DOCUMENTS

| | | | |
|---|---|---|---|
| 3,384,545 | 5/1968 | Aiello et al. | 514/938 X |
| 4,073,943 | 2/1978 | Wretlind et al. | 514/938 X |
| 4,719,239 | 1/1988 | Muller et al. | 514/938 X |
| 4,784,845 | 11/1988 | DeSai et al. | 514/938 X |
| 4,801,455 | 1/1989 | List et al. | 424/400 |
| 5,326,789 | 7/1994 | Narayanan | 514/383 X |

FOREIGN PATENT DOCUMENTS

| | | |
|---|---|---|
| 0 211 258 | 2/1987 | European Pat. Off. . |
| 0 315 079 | 5/1989 | European Pat. Off. . |
| 0 567 982 | 11/1993 | European Pat. Off. . |
| 87 01035 | 2/1987 | WIPO . |
| 91 07962 | 6/1991 | WIPO . |

*Primary Examiner*—Richard D. Lovering
*Attorney, Agent, or Firm*—Foley & Lardner

[57] ABSTRACT

An injectable oil-in-water emulsion composition comprises an antifungal triazole compound of the following formula (I)

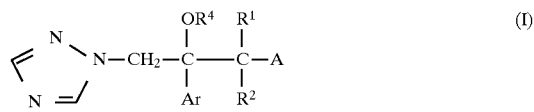

wherein Ar represents a substituted phenyl group; $R^1$ and $R^2$ represent, independently, a hydrogen atom or a lower alkyl group, or $R^1$ and $R^2$ may together form a lower alkylene group; $R^4$ represents a hydrogen atom or an acyl group; and A represents an optionally substituted cyclic amide group bonded through a nitrogen atom, or a salt thereof. The solubility of the triazole compound having poor water-solubility and fat-solubility can remarkably be increased by dispersing in water with use of an oil component (e.g. a triglyceride of fatty acids) and an emulsifier (e.g. a phospholipid).

13 Claims, 3 Drawing Sheets

INJECTABLE COMPOSITION AND A METHOD OF PRODUCING THE SAME

This application is a 371 of PCT/JP95/00260 filed Feb. 23, 1995.

TECHNICAL FIELD

The present invention relates to injectable compositions containing a triazole compound useful as antifungal therapeutic agents (antimycotics) and methods of producing the same.

BACKGROUND ART

Recently, there have been found increasing numbers of profunda fungal infections caused by fungi such as those belonging to the genus Candida, the genus Aspergillus and the genus Cryptococcus, specifically as a complication in, for example, a patient transplanted with an organ, a patient administered with a large quantity of an antibiotic, an anticancer drug (cartinostatic) or a steroidal agent in a long period, a patient suffering from AIDS, or a patient suffering from cancer in terminal stage ("Medical Mycology", Harukuni Urabe, Tadahiko Matsumoto and Shozo Motofusa, published on Jun. 10, 1993, Kanehara Publishing Co., Ltd., Japan). Against these profunda fungal infections, various azole drugs having antifungal functions or activities due to, for instance, inhibition of ergosterol synthesis in fungal cell membrane or disturbance of double membranes of the cell membrane have been researched and developed in 1980's, and some of these drugs have already been on the market (Hideyo Yama-guchi, Nippon Rinsho, 49, 2176–2185 (1991)).

There have been known, as triazole antifungal agents among azole antifungal agents, fluconazole, itraconazole, saperconazole, D0870 (1047, Abstract of the 1992 ICAAC) and so on. Further, a compound shown by the general formula (I) described in EP-A1-0567982 is expected as a novel triazole compound having antifungal activity.

These triazole compounds, however, generally have poor water-solubility, and therefore, can hardly be formulated into a composition for intravenous administration. Such drugs which are poorly or sparingly soluble in water can be solubilized by, for instance, solubilizing with a clathrate or inclusion compound such as cyclodextrin, dissolving in a water-soluble solvent such as polyethylene glycol, or solubilizing with using a surfactant such as polyoxyethylene hardened castor oil and the like. These liquid preparations, however, have been limited for an application as a medicine, since the solubilizing agent in itself has some toxicity and large quantity of such solubilizing agent is required in the preparations. Therefore, development of methods for preparing an injectable composition having higher safety is a principle problem in such triazole compounds.

The EP-A1-0567982, regarding to a pharmaceutical preparation (composition) containing the triazole compounds, discloses that the triazole compound can be formulated into an aqueous injection together with a dispersing agent, a preservative, an isotonic agent or the like, and that the compound can be formulated into an oily injection by dissolving, suspending or emulsifying in a plant oil (vegetable oil) such as soybean oil, propylene glycol and the like. In such triazole compounds having poor solubility not only in water but also in an oil, however, the drug concentration in an injection can hardly be increased.

EP-A1-315079 corresponding to Japanese Patent Application Laid-open No. 203/1990 (JP-A-2-203) discloses a drug carrier in the form of a fat emulsion, which contains a drug and has a mean particle diameter of less than 200 nm, preferably not less than 5 nm to less than 200 nm, and particularly preferably less than 100 nm. The drug carrier comprises a substance as the core and a substance as the surface layer of the emulsion. The core substance of the fat emulsion includes a simple lipid, a derived lipid, a drug itself or a mixture thereof, and a proportion of the core substance in the drug carrier is 30 to 85%. The substance constituting the surface layer of the fat emulsion is a complex lipid, a derived lipid, a drug itself or a mixture thereof and a ratio of the surface layer substances in the drug carrier is 15 to 70%.

WO91/07962 discloses an emulsion comprising (a) 0.001 to 10% (W/V) of an imidazole antifungal agent (miconazole), (b) 0.5 to 30% (W/V) of a simple lipid, (c) 0.05 to 2 times by weight as much a phospholipid as the simple lipid and (d) water, or a freeze dried preparation thereof. The literature describes that preferable mean particle diameter of the fat emulsion is not more than 500 nm, specifically not more than 100 nm.

EP-A2-0211258 corresponding to Japanese Patent Application Laid-open No. 29511/1987 (JP-A-62-29511) discloses a composition for parenteral administration consisting essentially of a microemulsion of a discontinuous phase component selected from pharmaceutically acceptable lipids, lipophilic drugs, and mixtures thereof dispersed in a sterile, non-pyrogenic aqueous continuous phase. The composition contains from about 0.6% to about 10% by weight of phospholipid as an emulsifier and have a droplet size such that less than 1% of the droplets have diameters greater than 125 nm. In the examples of the literature, the particle size of the discontinuous phase has a mean particle size of less than 100 nm.

WO87/01035 corresponding to Japanese Patent Application Laid-open No. 500456/1988 (JP-A-63-500456) teaches a composition for the administration of a fat-soluble active ingredient to an animal subject, which comprises pseudomicelles, wherein 90% of the pseudomicelles have diameters in the range of 1,000±300 Å.

Even when using these methods as above, however, the concentration of the triazole compound having poor solubility in an injection can hardly be increased. Further, the application of the methods to the triazole compound impairs the stability of the obtained emulsion. In particular, heat sterilization such as autoclave treatment extremely impairs the stability of the emulsion.

Accordingly, it is an object of the present invention to provide an injectable composition having an increased concentration of a triazole compound and a method of producing the same.

It is another object of the present invention to provide an injectable composition containing a triazole compound and having higher safety and a method of producing the composition.

A further object of this invention is to provide an injectable composition having higher dispersing stability in spite of being an emulsion comprising a triazole compound having poor water-solubility and fat-solubility, and a method of producing the same.

Yet another object of the present invention is to provide an injectable composition having higher dispersing stability even when subjected to heat sterilization, and a method of producing such composition.

It is a yet further object of the present invention to provide an injectable composition comprising an oil-in-water emulsion having higher content of a triazole compound having poor fat-solubility and higher dispersing stability of the dispersed system, whereby the triazole compound can effectively be administered intravenously, and a method of producing the composition.

DISCLOSURE OF THE INVENTION

Under the above mentioned circumstances, the present inventors made intensive investigations to find that the solubility of a specific triazole compound can remarkably be increased by an interaction of the triazole compound and a fine oil-in-water emulsion (hereinafter may simply referred to as emulsion). It is probably understood that such an interaction increases not only the solubility of the triazole compound in the oil phase of the emulsion but also the thermodynamic stability of the compound in the emulsion system due to attachment or joint of the triazole compound to an emulsifier in the interface of the oil phase and the water phase. They further found that pharmacological activities of the drug can effectively be exhibited without any side effect when the triazole compound is solubilized in such a manner and administered intravenously. Based on these findings and further investigations, the present invention has been accomplished.

Thus, the present invention relates to an injectable oil-in-water emulsion composition comprising an antifungal triazole compound of the following formula (I)

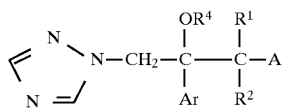

wherein Ar represents a substituted phenyl group; $R^1$ and $R^2$ represent, independently, a hydrogen atom or a lower alkyl group, or $R^1$ and $R^2$ may together form a lower alkylene group; $R^4$ represents a hydrogen atom or an acyl group; and A represents an optionally substituted cyclic amide group bonded through a nitrogen atom, or a salt thereof.

The cyclic amide group represented by A in the compound shown by the formula (I) may be an unsaturated cyclic amide group or a saturated cyclic amide group. The oil-in-water emulsion can be obtained by using an emulsifier. For instance, the oil-in-water emulsion can be prepared by dispersing a mixture of (1) a disperse phase comprising an oil component and an emulsifier and (2) a triazole compound shown by the formula (I) in water. As the oil component, for example, a glycerol ester of a fatty acid having 6 to 30 carbon atoms can be employed. Examples of the emulsifier include phospholipids such as lecithin. In spite of having poor solubility in an oil component, the concentration of the triazole compound in the disperse phase is high.

The disperse phase particles (discontinuous phase) are dispersed in water (continuous phase) with high stability. The mean (average) particle size can be selected from the range depending on the species of the triazole compound and so on, as far as the stability of dispersion is not adversely affected, and thus, for example, is from about 25 to 500 nm.

DETAILED DESCRIPTION OF THE INVENTION

Figure 1:
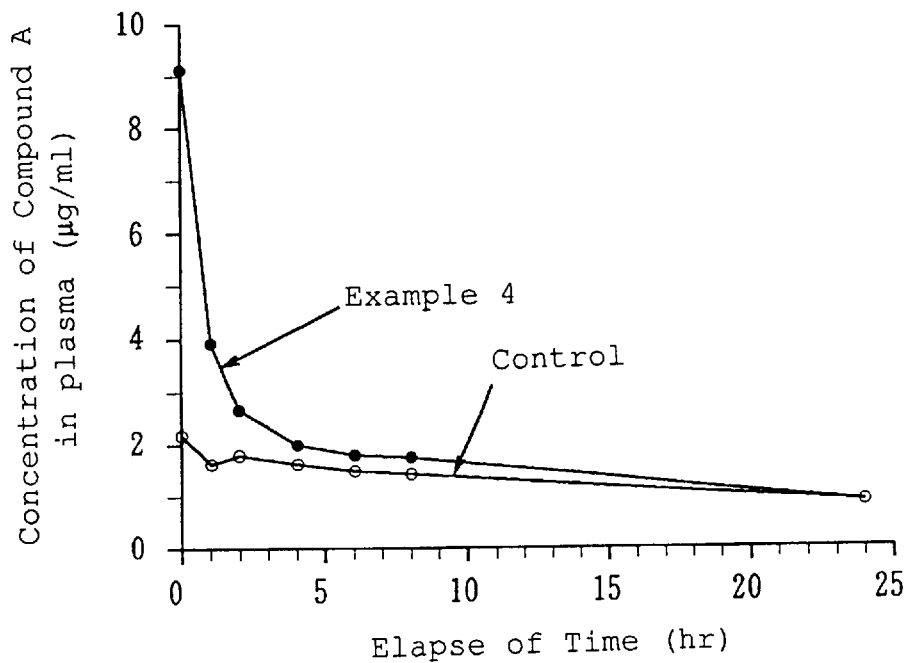
FIG. 1 is a graph illustrating the time-dependent change of the concentration of Compound A in Experimental Example 1.

The compounds shown by the formula (I) are illustrated hereinbelow.

Examples of the substituted phenyl group represented by Ar include a phenyl group having one to three substituents independently selected from a halogen atoms, a halogenated lower alkyl group, a halogenated lower alkoxy group (lower alkoxy halide group) and the like. The halogen atom includes a fluorine, chlorine, bromine and iodine atoms. Preferred example of the halogen atom includes a fluorine atom or a chlorine atom, specifically a fluorine atom. As the halogenated lower alkyl group, there may be mentioned, for example, a halogenated $C_{1-3}$ alkyl group such as fluoromethyl, difluoromethyl, trifluoromethyl, 2,2-difluoroethyl, 2,2,2-trifluoroethyl, 1,1,2,2-tetrafluoroethyl, pentafluoroethyl, 2,2,3,3-tetrafluoropropyl, 2,2,3,3,3-pentafluoropropyl group and chlorinated alkyl groups corresponding to these fluorinated alkyl groups. The halogenated lower alkoxy group includes, for instance, a halogenated $C_{1-3}$ alkoxy group such as fluoromethoxy, difluoromethoxy, trifluoromethoxy, 2,2-difluoroethoxy, 2,2, 2-trifluoroethoxy, 1,1,2,2-tetrafluoroethoxy, pentafluoroethoxy, 2,2,3,3-trifrafluoroproxy, 2,2,3,3,3-pentafluoropropoxy group and chlorinated alkoxy groups corresponding to these fluorinated alkoxy groups.

As examples of the substituted phenyl group, there may be mentioned 4-fluorophenyl, 4-chlorophenyl, 4-bromophenyl, 2-chlorophenyl, 2-fluorophenyl, 2-fluoro-4-chlorophenyl, 2-chloro-4-fluorophenyl, 2,4-difluorophenyl, 2,4-dichlorophenyl, 2,4,6-trifluorophenyl, 4-trifluoromethoxyphentyl groups.

Preferred example of the substituted phenyl group represented by Ar includes a phenyl group substituted with fluorine atom(s). Specifically preferred includes, for example, a phenyl group substituted with about 1 to 3, preferably about 1 or 2 fluorine atoms such as 2-fluorophenyl, 4-fluorophenyl, 2,4-difluorophenyl and the like.

The lower alkyl group represented by $R^1$ or $R^2$ in the formula (I) includes, for example, a straight or branched alkyl group having about 1 to 4 carbon atoms such as methyl, ethyl, propyl, isopropyl, butyl, isobutyl, s-butyl and t-butyl groups. Among these lower alkyl groups, an alkyl group having about 1 to 3 carbon atoms, especially a methyl group is preferred.

Preferred combinations of $R^1$ and $R^2$ include, for instance, combinations of hydrogen and hydrogen atoms; $C_{1-4}$ alkyl and $C_{1-4}$ alkyl groups; a hydrogen atom and a $C_{1-4}$ alkyl group and the like. Combinations of hydrogen and hydrogen atoms; a hydrogen atom and a methyl group; and methyl and methyl groups are specifically preferred. In typically preferred compounds of the formula (I), $R^1$ and $R^2$ are both hydrogen atoms, or one of $R^1$ and $R^2$ is a hydrogen atom and the other is a methyl group.

As examples of the lower alkylene group formed by $R^1$ and $R^2$, there may be mentioned a straight or branched lower $C_{2-4}$ alkylene group such as ethylene, trimethylene, propylene, butylene (tetramethylene) and other groups. An ethylene group may advantageously be employed among these alkylene groups.

The optionally substituted cyclic amido group bonded through a nitrogen atom represented by substituent A in the formula (I) may be an unsaturated cyclic amide group or a saturated cyclic amide group. The cyclic amide group has about 1 to 3 nitrogen atoms in the ring, and may further have one oxygen or sulfur atom in the ring. The cyclic amide group is a 4- to 8-membered and preferably 5- or 6-membered ring group.

The unsaturated cyclic amide group includes a group shown by the following formula (II)

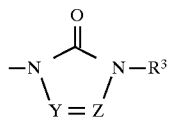
(II)

wherein $R^3$ represents a group bonded through a carbon atom; Y and Z independently represent a nitrogen atom or a methine group which may be substituted with a lower alkyl group.

As examples of the lower alkyl group which may be substituted on the methine group represented by Y and Z, there may be mentioned a straight or branched alkyl group having about 1 to 4 carbon atoms as mentioned in the explanation of $R^1$ and $R^2$. Preferred examples of the lower alkyl group include an alkyl group having about 1 to 3 carbon atoms, specifically a methyl group. In the typically preferred compounds, the methine group is not substituted with an alkyl group.

Examples of the saturated cyclic amide group include a group shown by the following formula (III).

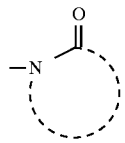
(III)

The saturated cyclic amide group has about 1 to 3 nitrogen atoms in the ring, and may further have about one oxygen or sulfur atom in the ring. The saturated cyclic amide group includes, for instance, 4- to 8-membered, and preferably 5- or 6-membered ring. As examples of such saturated cyclic amide group, there may be mentioned 2-oxo-1-imidazolidinyl, 5-oxo-1-imidazolidinyl, 2-oxo-1-pyrrolidinyl, 3-oxo-2-pyrazolidinyl, 2-oxo-1-piperazinyl, 2-oxo-1-piperidinyl, 3-oxomorpholino, 2-oxo-1-perhydropyrimidinyl and other groups.

The saturated cyclic amide group may preferably have two nitrogen atoms in the ring. Examples of such saturated cyclic amide group include 2-oxo-1-imidazolidinyl, 2-oxo-1-piperazinyl and 2-oxo-1-perhydropyrimidinyl groups.

As examples of the substituent(s) for the saturated cyclic amide group, there may be mentioned an oxo group, a halogen atom (e.g. fluorine, chlorine, bromine or iodine atom), the group bonded through a carbon atom represented by $R^3$ of the formula (II). The number of the substituents for the saturated cyclic amide group is, for example, about 1 to 3 and preferably about 1 or 2.

With respect to the formulae (II) and (III), the group bonded through a carbon atom represented by $R^3$ is exemplified with an aliphatic hydrocarbon group, an aromatic hydrocarbon group and an aromatic heterocyclic group, and these groups may be substituted with a substituent.

Examples of the aliphatic hydrocarbon group include an optionally substituted alkyl group, an optionally substituted cycloalkyl group, an optionally substituted alkenyl group and an optionally substituted alkynyl group. As the alkyl group, there may be mentioned, for instance, a straight or branched alkyl group having about 1 to 12 carbon atoms such as methyl, ethyl, propyl, isopropyl, butyl, isobutyl, s-butyl, t-butyl, hexyl, heptyl, octyl, nonyl, decyl, dodecyl and other groups. Among these alkyl groups, a lower alkyl group having about 1 to 4 carbon atoms (for example methyl, ethyl, propyl, isopropyl, butyl, isobutyl, s-butyl, t-butyl group, etc.) is preferred. The cycloalkyl group includes, for instance, a cycloalkyl group having about 3 to 8 carbon atoms such as cyclopropyl, cyclobutyl, cyclopentyl, cyclohexyl, cycloheptyl and cyclooctyl groups. A cycloalkyl group having about 3 to 6 carbon atoms such as cyclopropyl, cyclobutyl, cyclopentyl, cyclohexyl group and the like is preferable as the cycloalkyl group.

Examples of the alkenyl group include an alkenyl group having about 2 to 4 carbon atoms such as vinyl, propenyl and butenyl groups. As preferred examples of the alkenyl group, there may be mentioned an alkenyl group having about 2 or 3 carbon atoms such as vinyl and propenyl groups. The alkynyl group includes, for instance, an alkynyl group having about 2 to 4 carbon atoms such as ethynyl, propynyl, butynyl group and others. Among these alkynyl groups, an alkynyl group having about 2 or 3 carbon atoms (e.g. ethynyl, propynyl, etc.) is preferred.

As the aromatic hydrocarbon group, there may be mentioned, for example, an aryl group having about 6 to 14 carbon atoms such as phenyl, naphthyl, biphenylyl, anthryl and indenyl groups. Among these groups, an aryl group having about 6 to 10 carbon atoms (for instance, phenyl, naphthyl, etc.) or the like is preferred.

The aromatic heterocyclic group includes, for example, an aromatic heterocyclic group having at least one hetero atom selected from a nitrogen atom, a sulfur atom and an oxygen atom. The aromatic heterocyclic group may be a condensed aromatic heterocyclic group condensed with, for instance, a benzene ring, or a 5- or 6-membered heterocyclic ring. Examples of such heterocyclic group include an aromatic heterocyclic group such as imidazolyl, triazolyl, tetrazolyl, pyrazolyl, pyridyl, thiazolyl, thiadiazolyl, thienyl, furyl, pyrrolyl, pyrazinyl, pyrimidinyl, oxazolyl, isooxazolyl and the like; a condensed aromatic heterocyclic group such as benzimidazolyl, imidazopyrimidinyl, imidazopyridinyl, imidazopyrazinyl, imidazopyridazinyl, benzothiazolyl, quinolyl, isoquinolyl, quinazolinyl, indolyl and other groups. Typically preferred examples of the aromatic heterocyclic group include 5- or 6-membered aromatic heterocyclic group having 1 to 3 hetero atoms selected from a nitrogen atom, a sulfur atom and an oxygen atom (for instance, imidazolyl, triazolyl, thiazolyl, thiadiazolyl, thienyl, furyl, pyridyl or pyrimidinyl group).

As for $R^3$, examples of the substituent(s) for the aliphatic hydrocarbon group, the aromatic hydrocarbon group and the aromatic heterocyclic group include a hydroxyl group, an optionally esterified carboxyl group (e.g. carboxyl group, an alkoxycarbonyl group having about 2 to 7 carbon atoms such as methoxycarbonyl, ethoxycarbonyl, butoxycarbonyl and so on), a nitro group, an amino group, an acylamino group (for instance, an alkanoylamino group having about 1 to 10 carbon atoms such as acetylamino, propionylamino and butyrylamino groups), a mono- or di-alkylamino group wherein the amino group is mono- or di-substituted with alkyl group(s) having about 1 to 10 carbon atoms such as methylamino, dimethylamino, diethylamino, dibutylamino group, etc., an optionally substituted 5- or 6-membered cyclic amino group (for example, pyrrolidinyl, morpholino, piperidino, pyrazolidinyl, perhydroazepinyl, piperazinyl, 4-benzylpiperazinyl, 4-acetylpiperazinyl, 4-(4-trifluoromethoxyphenyl)-1-piperazinyl, 4-[4-(1,1,2,2-tetrafluoroethoxy)phenyl]-1-piperazinyl, 4-[4-(2,2,3,3-tetrafluoropropoxy)phenyl]-1-piperazinyl, 4-[4-(2,2,2-trifluoroethoxy)phenyl]-1-piperazinyl, 4-[(2,2,3,3,3-pentafluoropropoxy)phenyl]-1-piperazinyl, 4-(4-trifluoromethylphenyl)-1-piperazinyl and 4-(4-methoxyphenyl)piperazinyl groups), an alkoxy group having about 1 to 6 carbon atoms (e.g. methoxy, ethoxy, butoxy group and the like), a halogen atom (for example, fluorine, chlorine, or bromine atom), a halogenated alkyl group having about 1 to 6 carbon atoms (for instance, trifluoromethyl, dichloromethyl, trifluoroethyl and other groups), a halogenated alkoxy group having about 1 to 6 carbon atoms (e.g. trifluoromethoxy, 2-fluoroethoxy, 2,2-difluoroethoxy, 1,1,2,2-tetrafluoroethoxy, 2,2,2-trifluoroethoxy, 1,1,2,2-tetrafluoropropoxy, 2,2,3,3-tetrafluoropropoxy, 2,2,3,3,3-pentafluoropropoxy, perfluoropropoxy, 3,4,4-trifluorobutoxy, 3,3,4,4-tetrafluorobutoxy, 2,3,4,4,4-pentafluorobutoxy, 2,2,3,3,4,4,5,5-octafluoropentoxy group and the corresponding chlorinated alkoxy groups), an oxo group, a thioxo group, a mercapto group, an alkylthio group having about 1 to 6 carbon atoms (for example, methylthio, ethylthio, butylthio and other groups), an alkylsulfonyl group having about 1 to 6 carbon atoms (e.g. methanesulfonyl, ethanesulfonyl, butanesulfonyl group, etc.), an alkanoyl group having about 1 to 10 carbon atoms (for instance, formyl, acetyl, propionyl or butyryl group) and so on.

With respect to the substituent(s) for the saturated cyclic amide group represented by A, the optionally substituted aliphatic hydrocarbon group, the optionally substituted aromatic hydrocarbon group or the optionally substituted aromatic heterocyclic group is, preferably, bonded to a nitrogen atom constituting the broken line portion of the ring of the above-mentioned saturated cyclic amide group.

Preferred examples of A include (a) a non-substituted saturated cyclic amide group, (b) a saturated cyclic amide group substituted with an oxo group, (c) a saturated cyclic amide group substituted with a halogenated phenyl group, (d) a saturated cyclic amide group substituted with a halogenated phenyl group and an oxo group, (e) a saturated cyclic amide group substituted with a halogenated lower ($C_{1-6}$) alkyl-phenyl group, (f) a saturated cyclic amide group substituted with a halogenated lower ($C_{1-6}$) alkyl-phenyl group and an oxo group, (g) a saturated cyclic amide group substituted with a halogenated lower ($C_{1-6}$) alkoxy-phenyl group, (h) a saturated cyclic amide group substituted with a halogenated lower ($C_{1-6}$) alkoxy-phenyl group and an oxo group, and the like.

As examples of (a) the non-substituted saturated cyclic amide group, there may be mentioned 2-oxo-1-imidazolidinyl, 5-oxo-1-imidazolidinyl, 2-oxo-1-pyrrolidinyl, 3-oxo-2-pyrazolidinyl, 2-oxo-1-piperazinyl, 2-oxo-1-piperidinyl, 3-oxomorpholino, 2-oxo-1-perhydropyrimidinyl and other groups.

(b) The saturated cyclic amide group substituted with an oxo group includes, for example, 2,4-dioxo-1-imidazolidinyl, 2,5-dioxo-1-imidazolidinyl, 2,4-dioxo-1-pyrrolidinyl, 3,5-dioxo-2-pyrazolidinyl, 2,3-dioxo-1-piperazinyl, 2,5-dioxo-1-piperazinyl, 2,3-dioxo-1-piperidinyl group and so on.

The non-substituted saturated cyclic amide group and the saturated cyclic amide group substituted with an oxo group may, preferably, further have one of the second nitrogen atom in the ring other than the nitrogen atom bonded to the carbon atom to which $R^1$ and $R^2$ are bonded. Preferably, the second nitrogen atom may be combined with a substituent such as a halogenated phenyl group, a halogenated ($C_{1-6}$) alkyl-phenyl group, a halogenated ($C_{1-6}$) alkoxy-phenyl group or the like as explained hereafter.

As (c) the saturated cyclic amide group substituted with a halogenated phenyl group, there may be mentioned, for instance, a 3-halophenyl-2-oxo-1-imidazolidinyl, a 3-halophenyl-2-oxo-1-pyrrolidinyl, a 4-halophenyl-2-oxo-1-piperazinyl, a 4-halophenyl-2-oxo-1-piperidinyl group and others. Among these groups, specifically preferred includes a 3-halophenyl-2-oxo-1-imidazolidinyl group.

Examples of (d) the saturated cyclic amide group substituted with a halogenated phenyl group and an oxo group involve a 3-halophenyl-2,4-dioxo-1-imidazolidinyl, a 3-halophenyl-2,4-dioxo-1-pyrrolidinyl, a 4-halophenyl-2,5-dioxo-1-piperazinyl, a 4-halophenyl-2,3-dioxo-1-piperazinyl, a 4-halophenyl-2,3-dioxo-1-piperidinyl and other groups. A 3-halophenyl-2,4-dioxo-1-imidazolidinyl, a 4-halophenyl-2,5-dioxo-1-piperazinyl, a 4-halophenyl-2,3-dioxo-1-piperazinyl group and the like are preferred among these saturated cyclic amide groups.

(e) The saturated cyclic amide group substituted with a halogenated lower ($C_{1-6}$) alkyl-phenyl group may be exemplified with a 3-[halogenated ($C_{1-6}$) alkyl]phenyl-2-oxo-1-imidazolidinyl, a 3-[halogenated ($C_{1-6}$) alkyl]phenyl-2-oxo-1-pyrrolidinyl, a 4-[halogenated ($C_{1-6}$) alkyl]phenyl-2-oxo-1-piperazinyl, a 4-[halogenated ($C_{1-6}$) alkyl]phenyl-2-oxo-1-piperidinyl group and so on. Preferred example of these groups includes a 3-[halogenated ($C_{1-6}$) alkyl]phenyl-2-oxo-1-imidazolidinyl group and others.

As examples of (f) the saturated cyclic amide group substituted with a halogenated lower ($C_{1-6}$) alkyl-phenyl group and an oxo group, there may be mentioned a 3-[halogenated ($C_{1-6}$) alkyl]phenyl-2,4-dioxo-1-imidazolidinyl, a 3-[halogenated ($C_{1-6}$) alkyl]phenyl-2,4-dioxo-1-pyrrolidinyl, a 4-[halogenated ($C_{1-6}$) alkyl]phenyl-2,5-dioxo-1-piperazinyl, a 4-[halogenated ($C_{1-6}$) alkyl]phenyl-2,3-dioxo-1-piperazinyl, a 4-[halogenated ($C_{1-6}$) alkyl]phenyl-2,3-dioxo-1-piperidinyl group, etc. Preferred examples of such saturated cyclic amide group include a 3-[halogenated ($C_{1-6}$) alkyl]phenyl-2,4-dioxo-1-imidazolidinyl, a 4-[halogenated ($C_{1-6}$) alkyl]phenyl-2,5-dioxo-1-piperazinyl, a 4-[halogenated ($C_{1-6}$) alkyl]phenyl-2,3-dioxo-1-piperazinyl group and others.

Examples of (g) the saturated cyclic amide group substituted with a halogenated lower ($C_{1-6}$) alkoxy-phenyl group include a 3-[halogenated ($C_{1-6}$) alkoxy]phenyl-2-oxo-1-imidazolidinyl, a 3-[halogenated ($C_{1-6}$) alkoxy]phenyl-2-oxo-1-pyrrolidinyl, a 4-[halogenated ($C_{1-6}$) alkoxy]phenyl-2-oxo-1-piperazinyl, a 4-[halogenated ($C_{1-6}$) alkoxy]phenyl-2-oxo-1-piperidinyl and other groups. Among these groups, a 3-[halogenated ($C_{1-6}$) alkoxy]phenyl-2-oxo-1-imidazolidinyl group and so on are preferable.

(h) The saturated cyclic amide group substituted with a halogenated lower ($C_{1-6}$) alkoxy-phenyl group and an oxo group includes, for instance, a 3-[halogenated ($C_{1-6}$) alkoxy]phenyl-2,4-dioxo-1-imidazolidinyl, a 3-[halogenated ($C_{1-6}$) alkoxy]phenyl-2,4-dioxo-1-pyrrolidinyl, a 4-[halogenated ($C_{1-6}$) alkoxy]phenyl-2,5-dioxo-1-piperazinyl, a 4-[halogenated (C1-6) alkoxy]phenyl-2,3-dioxo-1-piperazinyl, a 4-[halogenated ($C_{1-6}$) alkoxy]phenyl-2,3-dioxo-1-piperidinyl group and so on. Among them, preferred examples include a 3-[halogenated ($C_{1-6}$) alkoxy]phenyl-2,4-dioxo-1-imidazolidinyl, a 4-[halogenated ($C_{1-6}$) alkoxy]phenyl-2,5-dioxo-1-piperazinyl and a 4-[halogenated ($C_{1-6}$) alkoxy]phenyl-2,3-dioxo-1-piperazinyl groups.

Typically preferred examples of the substituent A include (c) the saturated cyclic amide group substituted with a halophenyl group, (d) the saturated cyclic amide group substituted with a halophenyl group and an oxo group, (e) the saturated cyclic amide group substituted with a halogenated lower ($C_{1-6}$) alkyl-phenyl group, (f) the saturated cyclic amide group substituted with a halogenated lower ($C_{1-6}$) alkyl-phenyl group and an oxo group, (g) the saturated cyclic amide group substituted with a halogenated lower ($C_{1-6}$) alkoxy-phenyl group, (h) the saturated cyclic amide group substituted with a halogenated lower ($C_{1-6}$) alkoxy-phenyl group and an oxo group and so on.

In particular, the as substituent A, preferable use is made of a 3-halophenyl-2-oxo-1-imidazolidinyl group such as 3-(2,4-difluorophenyl)-2-oxo-1-imidazolidinyl, 3-(4-fluorophenyl)-2-oxo-1-imidazolidinyl, 3-(2-fluorophenyl)-2-oxo-1-imidazolidinyl group and others; a 3-[halogenated lower ($C_{1-4}$) alkyl]phenyl-2-oxo-1-imidazolidinyl group such as 3-(4-trifluoromethylphenyl)-2-oxo-1-imidazolidinyl group; a 3-[halogenated lower ($C_{1-4}$) alkoxy]phenyl-2-oxo-1-imidazolidinyl group such as 3-(4-trifluoromethoxyphenyl)-2-oxo-1-imidazolidinyl, 3-[4-(2,2,2-trifluoroethoxy)phenyl]-2-oxo-1-imidazolidinyl, 3-[4-(1,1,2,2-tetrafluoroethoxy) phenyl]-2-oxo-1-imidazolidinyl, 3-[4-(1,1,2,2,2-pentafluoroethoxy)phenyl]-2-oxo-1-imidazolidinyl, 3-[4-(2,3,3-trifluoropropoxy)phenyl]-2-oxo-1-imidazolidinyl, 3-[4-(1,1,2,2-tetrafluoropropoxy)phenyl]-2-oxo-1-imidazolidinyl, 3-[4-(2,2,3,3-tetrafluoropropoxy) phenyl]-2-oxo-1-imidazolidinyl, 3-[4-(2,2,3,3,3-pentafluoropropoxy)phenyl]-2-oxo-1-imidazolidinyl, 3-[4-(perfluoropropoxy)phenyl]-2-oxo-1-imidazolidinyl, 3-[4-(3,4,4-trifluorobutoxy)phenyl]-2-oxo-1-imidazolidinyl, 3-[4-(3,3,4,4-tetrafluorobutoxy)phenyl]-2-oxo-1-imidazolidinyl, 3-[4-(2,3,4,4,4-pentafluorobutoxy)phenyl]-2-oxo-1-imidazolidinyl, 3-[4-(3,3,4,4,4-pentafluorobutoxy) phenyl]-2-oxo-1-imidazolidinyl group and so on.

Practically preferred examples of the "optionally substituted saturated cyclic amide group bonded through a nitrogen atom" include a 2-oxo-1-imidazolidinyl group (especially, a 3-substituted phenyl-2-oxo-1-imidazolidinyl group) shown by the formula

(IIIa)

wherein $R^3$ has the same meaning as defined above, or a 2,5-dioxo-1-piperazinyl group (typically, a 4-substituted phenyl-2,5-dioxo-1-piperazinyl group) shown by the formula

(IIIb)

wherein $R^3$ has the same meaning as defined above.

The group bonded through a carbon atom represented by the substituent $R^3$ includes those as mentioned above. As preferred examples of the substituent represented by $R^3$, there may be mentioned an optionally substituted phenyl group, specifically a substituted phenyl group. Examples of the substituted phenyl group include a halogenated phenyl group, a halogenated ($C_{1-6}$) alkyl-phenyl group, a halogenated ($C_{1-6}$) alkoxyphenyl group and the like as exemplified as the substituent for the saturated cyclic amide group. As practically preferred examples of the substituent $R^3$, there may be mentioned a phenyl group having a halogenated alkoxy group, specifically a phenyl group having a fluorinated $C_{1-6}$ alkoxy group (among them, a fluorinated $C_{1-4}$ alkoxy group).

Examples of the acyl group represented by $R^4$ in the formula (I) include an acyl group derived from an organic carboxylic acid. Such acyl group includes, for instance, an alkanoyl group, preferably an alkanoyl group having about 1 to 7 carbon atoms such as formyl, acetyl, propionyl, butyryl, isobutyryl, pentanoyl, hexanoyl or heptanoyl group, more preferably an alkanoyl group having about 1 to 3 carbon atoms; an arylcarbonyl group, preferably an arylcarbonyl group having about 7 to 15 carbon atoms such as benzoyl and naphthalenecarbonyl groups, more preferably an arylcarbonyl group having about 7 to 11 carbon atoms; an alkoxycarbonyl group, preferably an alkoxycabonyl group having 2 to 7 carbon atoms such as methoxycarbonyl, ethoxycarbonyl, propoxycarbonyl, isopropoxycarbonyl, butoxycarbonyl, isobutoxycarbonyl, s-butoxycarbonyl, t-butoxycarbonyl group and others, and more preferably an alkoxycarbonyl group having about 2 to 4 carbon atoms; an aryloxycarbonyl group, preferably aryloxycarbonyl group having about 7 to 15 carbon atoms such as phenoxycarbonyl group, and more preferably an aryloxycarbonyl group having about 7 to 11 carbon atoms; an aralkylcarbonyl group, preferably an aralkylcarbonyl group having about 8 to 20 carbon atoms such as benzylcarbonyl, phenethylcarbonyl, phenylpropylcarbonyl, naphthylethylcarbonyl and other groups, and more preferably an aralkylcarbonyl group having about 8 to 14 carbon atoms, and the like. These acyl groups may be substituted with suitable 1 to 3 substituents. As examples of the suitable substituents, there may be mentioned halogen atoms, lower alkyl groups and hydroxyl groups.

Preferably, the acyl groups are those which can be hydrolyzed in vivo. Practical examples of the hydrolyzable acyl group in vivo include formyl, acetyl, benzoyl, benzylcarbonyl group and so on. The substituent $R^4$ in the preferable compounds of the formula (I) is practically a hydrogen atom or a $C_{1-6}$ acyl group. Preferred examples of these groups include a hydrogen atom.

The compound of the formula (I) may also be employed as a salt. Examples of the salt include pharmaceutically acceptable salts such as a salt with an inorganic acid including hydrochloric acid, hydrobromic acid, sulfuric acid, nitric acid, phosphoric acid and the like; and a salt with an organic acid including acetic acid, trichloroacetic acid, trifluoroacetic acid, tartaric acid, citric acid, fumaric acid, maleic acid, toluenesulfonic acid, methanesulfonic acid and others.

The compound shown by the formula (I) or a salt thereof has one or more asymmetric carbon(s) in the molecule and, therefore, there are two or more stereoisomers. Any of such stereoisomers as well as a mixture thereof is within a scope of the compound used in the present invention, and preferable examples include an optically active compound having (R,R)-configuration. When both of (1) the carbon atom being bonded with the substituted phenyl group represented by Ar and (2) the carbon atom being bonded with $R^2$ are chiral centers, the compound can be in any configurations of (R,R)-, (R,S)-, (S,R)- and (S,S)-configurations, and it is preferred that where $R^1$ is a hydrogen atom and $R^2$ is a methyl group, both of the carbon atoms, to which the substituted phenyl group represented by Ar and the substituent $R^2$ are bonded respectively, have (R)-configurations.

The antifungal triazole compound shown by the formula (I) is a compound having a triazole ring and exhibiting antifungal activities [Hiroshi Koda, Haru-yuki Mazaki: Clinics and Researches, 66, 1752 (1989), Hideyo Yamaguchi: Journal of Fungi, 31, 1 (1990)]. More practically, as examples of the triazole compound shown by the formula (I) [Hideyo Yamaguchi: Journal of Fungi, 31, 1 (1990)], there may be mentioned terconazole [J. Heeres et al., J. Med. Chem., 26, 611–613 (1983)], vibnazole [F. Dubini et al., J. Chemother., 2/1, 45–50 (1990)], itraconazole [Keiko Shimokawa, Chemical Therapeutic Region, 9, 1979–1982 (1993)], fluconazole [Hideyo Yamaguchi et al.: Jpn. J. Antibiotics, 42, 1 (1989)], saperconazole [J. V. Cutsem et al., DRUG OF THE FUTURE, 14, No. 12, 1187–1209 (1989)] and D0870 [1047, Abstract of the 1992, ICAAC]. As the triazole compound having antifungal activity, itraconazole, saperconazole and D0870 or a salt thereof, particularly itraconazole, can advantageously be employed among others.

These compounds as above are all known compounds, and can be prepared, obtained and used according to the literatures and sources which they are described.

As for the compounds of the formula (I) or a salt thereof, a compound shown by the following formula (IV) or (V) or a salt thereof is preferred:

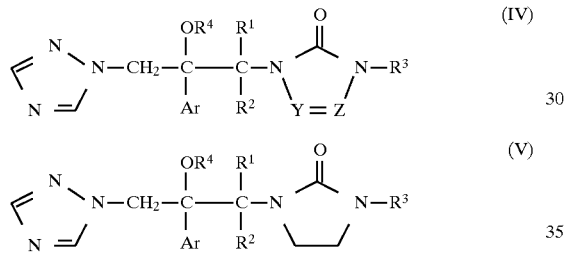

wherein Ar, $R^1$, $R^2$, $R^3$, $R^4$, Y and Z have the same meanings as defined above.

Particularly, preferred combinations of the substituents in the compound of the formula (I) or a salt thereof are as follows:

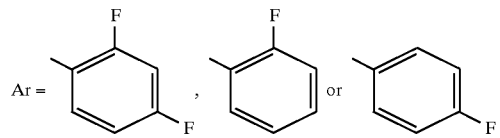

$R^1$ = $CH_3$
$R^2$ = H $R^3$ = —⟨phenyl⟩—OR (R: an alkyl group having 1 to 3 carbon atoms substituted with 1 to 4 fluorine atoms)

$R^4$ = H
Y = N or CH
Z = CH, C($CH_3$), N

Further, the following compounds, for instance, exhibit excellent antifungal activities among the compounds of the formula (I).

A 2-[(1R,2R)-2-(fluorinated phenyl)-2-hydroxy-1-methyl-3-(1H-1,2,4-triazol-1-yl)propyl]-4-[4-(fluorinated $C_{1-4}$ alkoxy)phenyl]-3(2H,4H)-1,2,4-triazolone such as (A) 2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone (herein briefly referred to as Compound A), etc.

A 1-[(1R,2R)-2-(fluorinated phenyl)-2-hydroxy-1-methyl-3-(1H-1,2,4-triazol-1-yl)propyl]-3-[4-(fluorinated $C_{1-4}$ alkoxy)phenyl]-2-imidazolidinone such as (B) 1-[(1R,2R)-2-(2,4-difluorophenyl)-2-hydroxy-1-methyl-3-(1H-1,2,4-triazol-1-yl)propyl-3-[4-(2,2,3,3-tetrafluoropropoxy)phenyl]-2-imidazolidinone (hereinafter referred to as Compound B), (C) 1-[(1R,2R)-2-(2,4-difluorophenyl)-2-hydroxy-1-methyl-3-(1H-1,2,4-triazol-1-yl)propyl]-3-[4-(1,1,2,2-tetrafluoroethoxy)phenyl]-2-imidazolidinone (herein briefly referred to as Compound C), (D) 1-[(1R,2R)-2-(2-fluorophenyl)-2-hydroxy-1-methyl-3-(1H-1,2,4-triazol-1-yl)propyl]-3-[4-(1,1,2,2-tetrafluoroethoxy)phenyl]-2-imidazolidinone (hereinafter referred to as Compound D), (E) 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2-imidazolidinone (hereinafter referred to as Compound E) and so on.

Preferred examples also include the following compounds:

(A1) 2-[(1R,2R)-2-(2,4-difluorophenyl)-2-hydroxy-1-methyl-3-(1H-1,2,4-triazol-1-yl)propyl]-4-[4-(1,1,2,2-tetrafluoroethoxy)phenyl]-3(2H,4H)-1,2,4-triazolone, (A2) 2-[(1R,2R)-2-(2-fluorophenyl)-2-hydroxy-1-methyl-3-(1H-1,2,4-triazol-1-yl)propyl]-4-[4-(1,1,2,2-tetrafluoroethoxy)phenyl]-3(2H,4H)-1,2,4-triazolone, (A3) 2-[(1R,2R)-2-(2-fluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, and the like.

In the compounds of the formula (I), the compound shown by the formula (IV) can be prepared according to the method described in EP-A1-0567982 or those analogous thereto, and can be used as a drug. The compound of the formula (IV) or its salt has higher antifungal activity as mentioned in the literature.

The compound of the formula (I) where A is a group shown by the formula (III) can be prepared by, for example, following manner.

For instance, the compound where A is the group shown by the formula (III) can be prepared by allowing a compound of the formula (VI)

wherein Ar, $R^1$, $R^2$ and A have the same meanings as defined above, to react with a compound of the formula (VII)

or a salt thereof, and if required, treating the resultant compound with an acylating agent.

The reaction may usually be carried out in a solvent whereby the reaction is not adversely affected. As examples of such solvent, there may be mentioned water; ketones such as acetone and methyl ethyl ketone; sulfoxides such as dimethylsulfoxide; ethers such as diethyl ether, tetrahydrofuran and dioxane; nitrites such as acetonitrile; aromatic hydrocarbons such as benzene, toluene and xylene; halogenated hydrocarbons such as dichloromethane, chloroform, 1,2-dichloroethane and others; esters such as ethyl acetate; amides such as dimethylformamide, acetamide, dimethylacetamide, 1-methyl-2-pyrrolidinone, etc.; ureylenes such as 1,3-dimethyl-2-imidazolidinone and the like. These solvents can be used alone or in combination with suitable mixing ratio.

The reaction is preferably conducted in the presence of a base. Examples of the base include alkali metal hydroxides such as lithium hydroxide, potassium hydroxide and sodium hydroxide; alkali metal hydrides such as potassium hydride and sodium hydride; alkali metal carbonates such as lithium carbonate, sodium carbonate, cesium carbonate, potassium carbonate, sodium hydrogencarbonate and the like; alkali metal salts with an organic acid such as sodium acetate and so on; alkali metal alcoholates such as sodium methylate, sodium ethylate, potassium t-butylate, etc.; tetrabutylammonium fluoride; bis(tri-n-butylstannyl) oxide and so on.

The compound of the formula (VII) may be used as a free compound, or a salt of a metal (for instance, a salt of an alkali metal such as sodium, potassium, etc.) of the compound of the formula (VII), instead of the compound (VII) can also be used to prepare the objective compound by conducting the reaction in the solvent.

The amount of the base is usually about 0.001 to 100 equivalents and preferably about 0.01 to 50 equivalents relative to the compound of the formula (VI).

The compound of the formula (VII) or its salt is generally used in a proportion of about 1 to 100 equivalents and preferably about 1 to 50 equivalents relative to the compound of the formula (VI).

The reaction temperature is not particularly restricted, and is usually about 0° C. to 150° C. and preferably about 10° C. to 120° C. The reaction can be carried out for several minutes to several ten hours (e.g. 5 minutes to 50 hours).

The compound where the substituent A is the group of the formula (III) can also be prepared by allowing a compound shown by the formula (VIII)

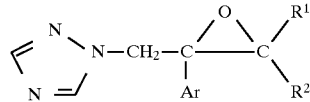  (VIII)

wherein Ar, $R^1$ and $R^2$ have the same meanings as defined above, or a salt thereof to react with a compound shown by the formula (IX)

H—A  (IX)

wherein A has the same meaning as defined above, or a salt thereof. According to this reaction, the compound of the formula (I) where $R^4$ is a hydrogen atom can be obtained.

The reaction may usually be conducted in an inert solvent whereby the reaction is not adversely affected. Examples of such solvent include water; ketones such as acetone and methyl ethyl ketone; sulfoxides such as dimethylsulfoxide; ethers such as diethyl ether, tetrahydrofuran and dioxane; nitriles such as acetonitrile; aromatic hydrocarbons such as benzene, toluene and xylene; halogenated hydrocarbons such as dichloromethane, chloroform, 1,2-dichloroethane and others; esters such as ethyl acetate; amides such as dimethylformamide, acetamide, dimethylacetamide, 1-methyl-2-pyrrolidinone, etc.; ureylenes such as 1,3-dimethyl-2-imidazolidinone and the like. These solvents can be used singly or in combination with suitable mixing ratio.

It is preferred that the reaction is carried out in the presence of a base. Examples of the base include alkali metal hydroxides such as lithium hydroxide, potassium hydroxide and sodium hydroxide; alkali metal hydrides such as potassium hydride and sodium hydride; alkali metal carbonates such as lithium carbonate, cesium carbonate, potassium carbonate, sodium carbonate, sodium hydrogencarbonate and the like; alkali metal salts with an organic acid such as sodium acetate and so on; alkali metal alcoholates such as sodium methylate, sodium ethylate, potassium t-butylate, etc.; tetrabutylammonium fluoride; bis(tri-n-butylstannyl) oxide and so on. Preferred base includes, for example, tetrabutylammonium fluoride and the like.

The compound of the formula (IX) may be employed as a free compound, or as a metal salt thereof (for example, a salt of an alkali metal such as sodium and potassium) to give the desired compound by the reaction in the presence of the solvent.

The proportion of the base is, for instance, about 0.001 to 100 equivalents and preferably about 0.01 to 50 equivalents relative to the compound of the formula (IX).

The compound of the formula (IX) or its salt is used in an amount of about 0.1 to 100 equivalents and preferably about 0.1 to 50 equivalents relative to the compound of the formula (VIII).

The reaction temperature is not specifically restricted, and is, usually, about 0° C. to 150° C. and preferably about 10° to 120° C. The reaction time is, for instance, in the range of about several minutes to several ten hours (e.g. from 5 minutes to 50 hours).

The compound of the formula (I) where A is an optionally substituted 2-oxo-1-imidazolidinyl group or a salt thereof may be obtained by, for instance, subjecting a compound shown by the following formula (X) or a salt thereof to catalytic reduction:

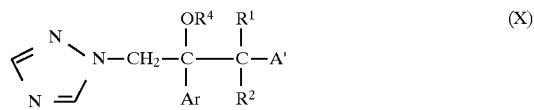  (X)

wherein A' represents an optionally substituted 2-oxo-2,3-dihydro-1H-imidazol-1-yl group, and Ar, $R^1$, $R^2$ and $R^4$ have the same meanings as defined above.

This reaction may be carried out in the presence of a solvent such as water or an inert organic solvent. The organic solvent includes, for example, ketones (for example, acetone, methyl ethyl ketone and the like), alcohols (e.g. methanol, ethanol, propanol, isopropanol, butanol, etc.), esters (for instance, ethyl acetate and so on), hydrocarbons (e.g. benzene, toluene, xylene, hexane, cyclohexane, etc.), organic carboxylic acids (for example, acetic acid or propionic acid) and the like. These organic solvents can be used singly or in combination.

The reaction is usually carried out in the presence of a catalyst. As such catalyst, a suitable catalyst for catalytic reduction such as palladium-carbon, palladium black, Raney nickel, platinum, platinum oxide and the like can be used. The reducing reaction may be conducted under a pressure from atmospheric pressure to about 150 kg/cm², at a temperature from room temperature to about 100° C.

As the salts of the starting compounds of the formula (VII), (VIII) and (X), those as exemplified for the compound of the formula (I) can be employed.

When a compound of the formula (I) where $R^4$ is a hydrogen atom is obtained respectively in the above reactions, the resultant compound or a salt thereof can be induced, in accordance with a conventional manner, to a compound of the formula (I) where $R^4$ is an acyl group by treating with a suitable acylating agent shown by the formula: $R^4X$ wherein $R^4$ represents an acyl group and X represents a leaving group which can be left in the reaction. The acyl group include groups as mentioned in the explanation of $R^4$, for example, a carboxylic acid residue such as acetyl, propionyl, butyryl, ethoxycarbonyl, benzoyl, substituted benzoyl and others. The leaving group represented by X includes, for instance, a halogen atom such as chlorine, bromine, etc., an active ester group and so on.

The reaction may generally be conducted in the absence or presence of an inert solvent. The solvent is exemplified with ketones such as acetone and methyl ethyl ketone; sulfoxides such as dimethylsulfoxide; ethers such as diethyl ether, tetrahydrofuran and dioxane; nitriles such as acetonitrile; aromatic hydrocarbons such as benzene, toluene and xylene; halogenated hydrocarbons such as dichloromethane, chloroform, 1,2-dichloroethane and others; esters such as ethyl acetate; amides such as dimethylformamide, acetamide and dimethylacetamide; ureylenes such as 1,3-dimethyl-2-imidazolidinone and the like. For acceleration of the reaction rate, a base such as dimethylaminopyridine, pyridine, pyrroline, trimethylamine, triethylamine or others may be added to the reaction system.

The compound of the formula (I) thus obtained can be isolated from the reaction mixture by conventional isolation and purification procedure such as extraction, concentration, neutralization, filtration, recrystallization, column chromatography and thin layer chromatography.

The compound of the formula (I) may have at least two stereoisomers. Each of such isomers and mixtures thereof are included in the scope of the compounds used in the present invention. If desired, each of such an isomer may be prepared separately. For instance, a single isomer of the compound can be obtained by the above reaction with the use of each single isomer of the starting compounds of the formula (VI), (VIII) and (X). When the product is a mixture of two or more of isomers, they may be separated into each isomer by conventional separating methods such as a method of producing a salt with an optically active acid (for example, camphorsulfonic acid or tartaric acid) or by means of various chromatographies, fractional recrystallization and so on.

The salt of the compound of the formula (I) may also be prepared by a conventional method such as by adding the above-mentioned inorganic or organic acid to the compound of the formula (I).

With regard to the starting compound of the formula (IV), the compound of the formula (XI) where $R^1$ is a hydrogen atom and $R^2$ is a methyl group, the carbon being bonded with Ar is in (S)-configuration, and the carbon being bonded with $R^2$ is in (R)-configuration, can be prepared, for example, by a method as given in the following scheme:

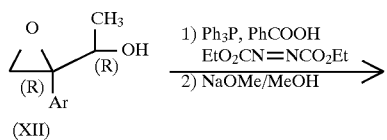
(XII)

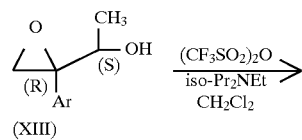
(XIII)

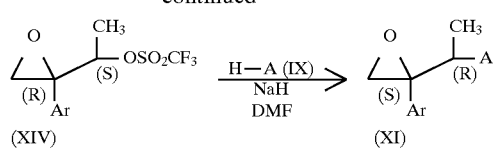

wherein Me is a methyl group, Et is an ethyl group, Pr is a propyl group, Ph is a phenyl group, DMF is a dimethylformamide, and Ar and A have the same meanings as defined above.

The starting compound of the formula (XII) in the scheme may be prepared, for instance, by a method as shown in the following scheme:

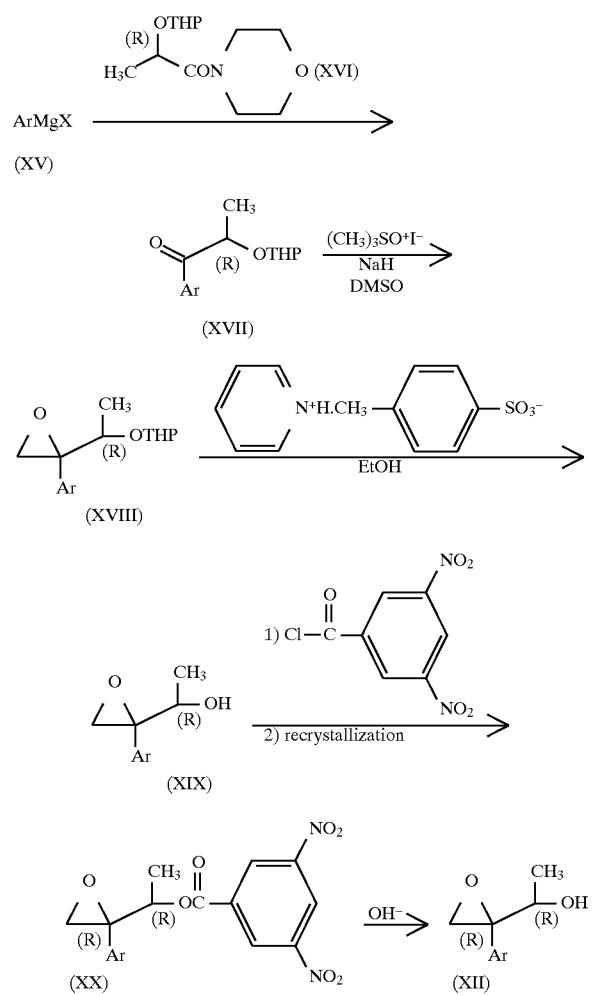

wherein THP represents a tetrahydropyranyl group, DMSO is dimethylsulfoxide, and Ar and Et have the same meanings as defined above.

In the starting compound of the formula (X) in the scheme, the compound (XXI) where $R^1$ is a hydrogen atom, $R^2$ is a methyl group, $R^4$ is a hydrogen atom and both of (1) the carbon atom being bonded with Ar and (2) the carbon atom being bonded with $R^2$ are in (R)-configurations, may be obtained by, for example, a method as given in the following scheme.

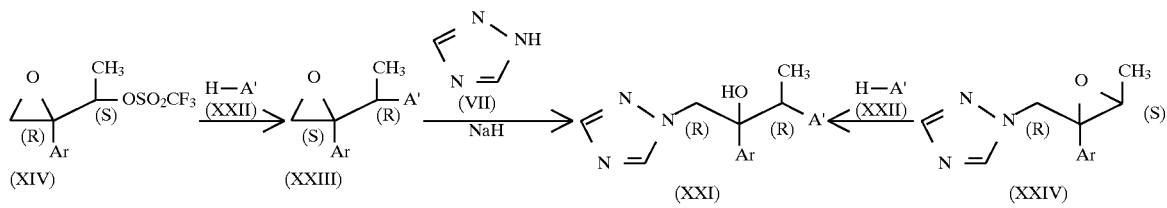

In the scheme, Ar and A' have the same meanings as defined above.

The starting compound (XXIV) in the scheme can be prepared according to, for instance, the method described in EP-A-0548553 or EP-A-0421210 or those analogous thereto.

The compound of the formula (XXV) which is the starting compound of the formula (XXII) in the scheme where A' is a 2-oxo-2,3-dihydro-1H-imidazol-1-yl group having a substituent on the 3-position may be prepared by for example a method as shown in the following scheme:

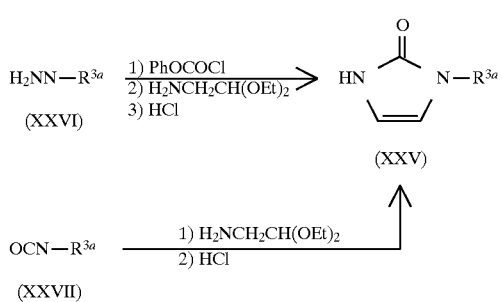

wherein $R^3a$ represents a substituent for A, and Ph and Et have the same meanings as defined above.

The compound of the formula (XXVIII) which is a compound of the formula (IX) where A is a 2-oxo-1-imidazolidinyl group having a substituent on the 3-position may be obtained by, for instance, a method as illustrated in the following scheme.

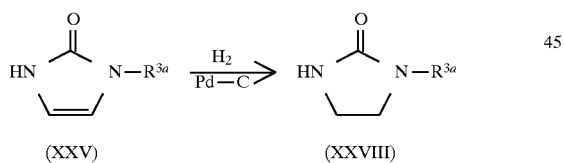

In the scheme, $R^{3a}$ has the same meaning as defined above.

Further, the compound of the formula (IX) where A is a 2,5-dioxo-1-piperazinyl group having a substituent on the 4-position, that is a compound of the formula (XXIX) can for example be prepared by a method as shown in the following scheme:

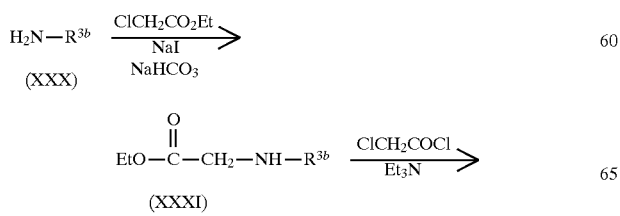

-continued

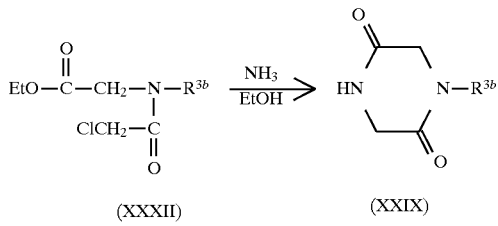

wherein $R^{3b}$ represents a substituent for A, and Et has the same meaning as defined above.

The compound of the formula (XXXIII) which is a compound of the formula (IX) where A is a 2,3-dioxo-1-piperazinyl group having a substituent on the 4-position can be obtained by, for instance, a method as illustrated in the following scheme:

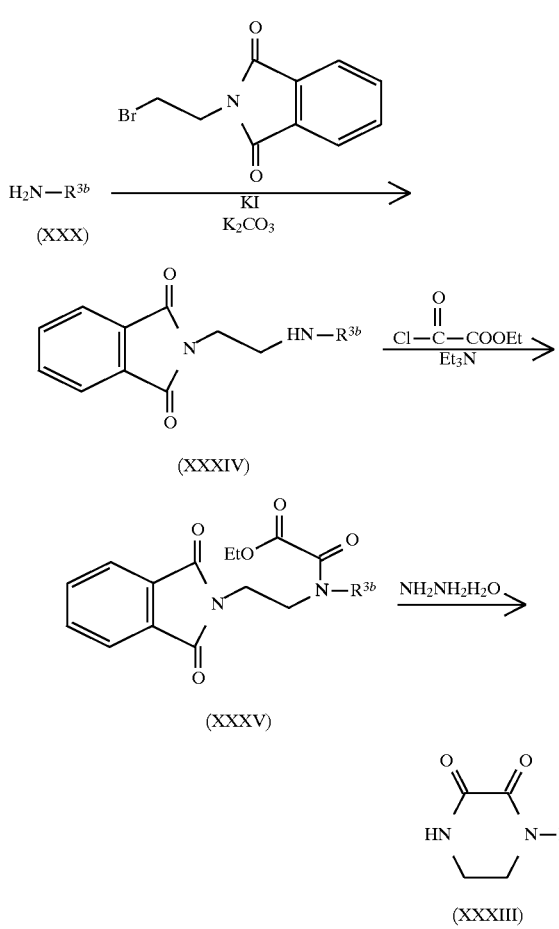

wherein $R^{3b}$ and Et have the same meanings as defined above.

The intermediate compound of the formula (XIII) can also be prepared by a method as exemplified in the following scheme:

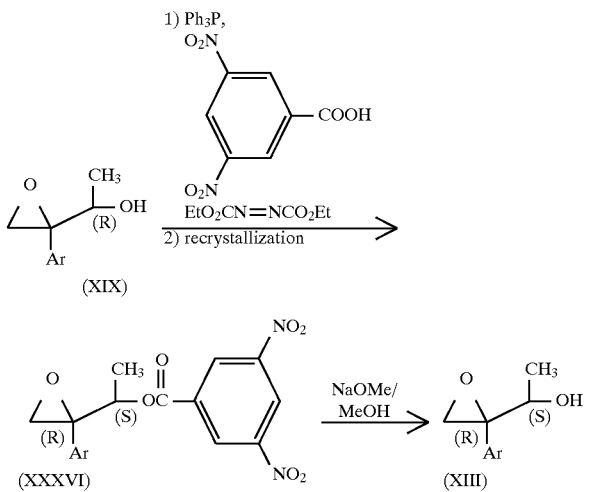

wherein Ar, Ph, Et and Me have the same meanings as defined above.

Each of the starting compounds as described above can be isolated from the reaction mixture by using a conventional isolation and purification procedure such as extraction, concentration, neutralization, filtration, column chromatography, thin layer chromatography or the like.

The triazole compound used in this invention has low toxicity and potent antifungal activities with broad antifungal spectrum, being effective to fungi such as those belonging to the genus Candida (for example, *Candida albicans, Candida utilis, Candida glabrata* and the like), the genus Aspergillus (e.g. *Aspergillus niger, Aspergillus fumigatus*, etc.), the genus Cryptococcus (for example, *Cryptococcus neoformans*, etc.), the genus Trichophyton (for instance; *Trichophyton rubrum, Trichophyton mentagrophytes* and so on), the genus Microsporum (e.g. *Microsporum gypseum*, etc.) and the like. Therefore, the injectable composition of the present invention can be used for prevention and therapy of fungal infections (e.g. candidosis, histoplasmosis, aspergillosis, cryptococcosis, trichophytosis, microsporumosis and so on) of mammals such as human beings, domestic animals or fowls. Further, the injectable composition of the invention can also be used as an antifungal agent for agricultural use. Moreover, the starting compound of the formula (X) where $R^4$ is a hydrogen atom for the production of the compound of the formula (I) used in this invention has also antifungal activities against the fungi as mentioned above.

According to the present invention, although having poor water-solubility and fat-solubility, the antifungal triazole compound shown by the formula (I) can effectively be used as a component of an injectable composition composed of an oil-in-water emulsion. The injectable composition of the present invention is composed of an oil-in-water emulsion comprising the triazole compound of the formula (I) or a salt thereof, wherein the triazole compound is dissolved in the oil-in-water emulsion.

The oil-in-water emulsion may be prepared by using an emulsifier, and comprises (1) a disperse phase particle comprising an oil component, an emulsifier and the triazole compound and (2) water where the disperse phase particle is dispersed therein.

As the oil component, any pharmaceutically acceptable fats and oils generally used in the preparation of a fat emulsion in the field of pharmaceutical technology. Examples of the fats and oils include vegetable oils (plant oils), oils obtainable by partial hydrogenation of vegetable oils, oils obtainable by transesterification (simple glycerides or mixed glycerides) and glycerol esters of fatty acids each having a medium-size chain.

The fats and oils include, for instance, a glycerol ester of a fatty acid having about 6 to 30 carbon atoms, preferably about 6 to 22 carbon atoms. As examples of the fatty acid, there may be mentioned saturated fatty acids such as caproic acid, caprylic acid, capric acid, lauric acid, myristic acid, palmitic acid, stearic acid and behenic acid; unsaturated fatty acids such as palmitooleic acid, oleic acid, linoleic acid, arachidonic acid, icosapentaenoic acid, docosahexaenoic acid and others.

Preferred examples of the fats and oils include vegetable oils such as soybean oil, cottonseed oil, rapeseed oil, peanut oil, safflower oil, sesame oil, rice bran oil, corn germ oil, sunflower oil, poppy oil, and olive oil. Soybean oil or the like may preferably be used among these vegetable oils.

A triglyceride of fatty acids each having a medium-size chain with about 6 to 14, preferably about 8 to 12 carbon atoms may also be employed as the fats and oils. As preferred triglyceride of a fatty acid having a medium-size chain, there may be mentioned a tri(capric acid/caprylic acid) glyceryl ester such as, for example, "Migriol 810" and "Migriol 812" (both trade names, manufactured by Huls Co., Ltd., available from Mitsuba Trading Co., Ltd.), a glyceryl tricaprylate (tricaprylin) such as "Panasate 800" (trade name, manufactured by Nippon Yushi Co., Ltd., Japan) and so on.

The proportion of the oil component based on the total amount of the oil-in-water emulsion is, for instance, about 1 to 30% by weight, preferably about 2 to 25% by weight and more preferably about 2.5 to 20% by weight.

The injectable composition of the present invention is characterized in that the solubility of the triazole compound having poor water-solubility and fat-solubility can extremely be increased by using an emulsifier in addition to the oil component in comparison with the case using only the oil component.

Any pharmaceutically acceptable emulsifiers can be used as the emulsifier. In particular, pharmaceutically acceptable phospholipids and nonionic surfactants can advantageously be used as the emulsifier. These emulsifiers may be employed singly or in combination.

Examples of the phospholipids include naturally-occurring phospholipids such as yolk lecithin, soybean lecithin and hydrogenated products thereof, or synthetic phospholipids such as phosphatidylcholines and phosphatidylethanolamines. Among these phospholipids, yolk lecithin, soybean lecithin and phosphatidylcholines obtainable from yolk and soybean are preferable. Lecithin can specifically preferably be used as the phospholipid.

As the nonionic surfactants, there may be mentioned, for instance, polymer surfactants having molecular weights of 800 to 20,000 such as a polyoxyethylene-polyoxypropylene copolymer, a polyoxyethylene alkyl ether, a polyoxyethylene alkylaryl ether, a polyoxyethylene hardened castor oil derivative, a polyoxyethylene sorbitan derivative, a polyoxyethylene sorbitol derivative, polyoxyethylene alkyl ether sulfate and the like.

The amount of the emulsifier is about 0.1 to 10% (W/V), preferably about 0.2 to 7% (W/V) and more preferably about 0.5 to 5% (W/V) based on the total volume of the oil-in-water emulsion.

The emulsifier is used in a proportion of about 0.1 to 150% by weight, preferably about 0.5 to 125% by weight and more preferably. about 1 to 100% by weight relative to the total weight of the oil component. Practically preferable amount of the emulsifier is about 1 to 15% by weight, and specifically about 1 to 10% weight relative to the total weight of the oil component.

The injectable composition of the present invention may be prepared by mixing a disperse phase comprising the triazole compound (active component), the oil component and the emulsifier with water. If necessary, an additive such as stabilizers for improving the stability of the active ingredient, isotonic agents for controlling the osmotic pressure, emulsifying-auxiliaries for improving the emulsifying power, emulsion-stabilizers for improving the stability of the emulsifier may be added to the injectable composition.

Example of the stabilizers for the active ingredient include antioxidants such as ascorbic acid, tocopherol, sorbic acid and retinol, chelating agents such as citric acid and tartaric acid, and the like. The amount of the stabilizer is, for example, about 0.00001 to 10% (W/V) and preferably about 0.0001 to 5% (W/V) based on the total volume of the injectable composition (injection).

The isotonic agents include, for. instance, glycerol, sugar-alcohols, monosaccharides, disaccharides, amino acids, dextran, albumin and others. Such isotonic agents may be employed either singly or in combination.

Examples of the emulsifying-auxiliaries include fatty acids having about 6 to 30 carbon atoms, salts of these fatty acids, monoglycerides of the fatty acids. Such fatty acids include, for example, caproic acid, caprylic acid, capric acid, lauric acid, myristic acid, palmitic acid, stearic acid, behenic acid, palmitooleic acid, oleic acid, linoleic acid, arachidonic acid, icosapentaenoic acid, docosahexaenoic acid and others. Salt of the fatty acid includes, for instance, an alkali metal salt such as a sodium salt and potassium salt, a calcium salt and the like.

As examples of the emulsifying stabilizer, there may be mentioned cholesterol, cholesterol esters, tocopherol, albumin, fatty acid amide derivatives, polysaccharides, derivatives of fatty acid esters of polysaccharides.

The content (concentration) of the triazole compound in the injectable composition of the present invention depends on the pharmacological activities or kinetics in blood of the compound, and is usually about 0.0001 to 2% (W/V), preferably about 0.005 to 1% (W/V) and more preferably about 0.01 to 0.5% (W/V) based on the total volume of the oil-in-water emulsion. The proportion of the triazole compound based on the total weight of the disperse phase comprising the oil component and the emulsifier is, for example, about 0.0001 to 2% by weight, preferably about 0.01 to 1.7% by weight and more preferably about 0.05 to 1.5% by weight.

The injectable composition of the present invention may principally be prepared according to a conventional method, or a method analogous thereto. The emulsification can be conducted in a conventional emulsifying technique, and, particularly, it is preferred to disperse or dissolve the triazole compound in the oil component beforehand. For example, the injectable composition composed of an oil-in-water emulsion may be prepared by dispersing a mixture of (1) a disperse phase comprising the oil component and the emulsifier and (2) the triazole compound of the formula (I) having antifungal activity in water.

Preferred examples of the method include a method which comprises homogenizing a heterogeneous mixture of (a) a mixture comprising the active ingredient, the oil component, the emulsifier, and if necessary, an additive such as an isotonic agent and (b) water with the use of an emulsifying apparatus (homogenizer) to give a roughly emulsified emulsion (rough emulsion), followed by, if necessary, adding water, further homogenizing the resultant rough emulsion with using the emulsifying apparatus and removing a particle having a larger particle size by a filtrating means such as a filter to give an injectable oil-in-water emulsion composition. The active ingredient may practically be dissolved or dispersed in the mixture by heating to a temperature of about 30° to 90° C., preferably about 40° to 80° C. As the emulsifying apparatus, a conventional apparatus such as a homogenizer including a pressure jetting homogenizer and an ultrasonic homogenizer, a homomixer including a high-rate mixer and the like. For removing a particle having a larger particle size of not less than 5 $\mu$m, preferably not less than 1 $\mu$m and more preferably not less than 0.5 $\mu$m, the homogenized emulsion may frequently be subjected to a filtrating means such as a filter.

In the injectable oil-in-water emulsion composition of the present invention, the mean particle size of the disperse phase is, for example, about 0.01 to 5 $\mu$m (10 to 5,000 nm), preferably about 0.02 to 1 $\mu$m (20 to 1,000 nm), more preferably about 0.03 to 0.5 $\mu$m (30 to 500 nm), and practically, about 0.02 to 0.2 $\mu$m (20 to 200 nm). In preferred injectable composition, the average or mean particle size of the disperse phase where the antifungal triazole compound is dissolved therein is about 30 to 250 nm, preferably about 50 to 250 nm (for example about 100 to 250 nm) and more preferably about 110 to 250 nm (e.g. about 120 to 230 nm).

Particularly, as for the injection comprising the triazole compound of the formula (IV) where the cyclic amide group represented by A is the unsaturated cyclic amide group of the formula (II), it is preferred that a disperse phase particle having a mean particle size of about 110 to 250 nm, preferably about 115 to 225 nm and more preferably about 120 to 200 nm is dispersed in water. In the injectable composition comprising the triazole compound where the cyclic amide group represented by A is the saturated cyclic amide group shown by the formula (III), especially by the formula (IIIa), the disperse phase particle is preferably dispersed in a mean particle size of about 140 to 250 nm, preferable about 150 to 230 nm and more preferably about 160 to 220 nm. From a viewpoint of the stability of and the in vivo distribution after administration of the emulsion, the mean (average) particle size (diameter) of the disperse phase particle is for example about 25 to 500 nm, preferably about 50 to 300 nm and more preferably about 90 to 250 nm (particularly about 110 to 250 nm).

The injectable composition of the present invention which comprises an oil-in-water emulsion increases the concentration of the antifungal triazole compound shown by the formula (I) or a salt thereof, and can be intravenously administered. Further, since the composition requires no solubilizing agent, it has scarcely local irritation and toxicity, and thus having remarkably mitigated hemolytic property and increased safety in comparison with a solution composition (aqueous injection) obtained by using a solubilizing agent.

Furthermore, the composition has improved dispersing stability even when subjected to heat sterilization. Moreover, by controlling the size of the oil particle in the emulsion, the emulsion has higher disperse stability in spite of comprising the triazole compound having poor solubilities in water and in an oil, and thus improving the in vivo kinetics and in vivo distribution of the drug to realize the targeting of the drug. Therefore, the composition can be applied to more effective therapy or treatment.

According to the method of the present invention, despite that the antifungal triazole compound of the formula (I) has poor water-solubility and fat-solubility (liposolubility), an injectable composition having excellent characteristics as above can be prepared by a simple and easy manner of emulsification or dispersion.

INDUSTRIAL APPLICABILITIES OF THE INVENTION

According to the injectable composition of the present invention, the concentration of the triazole compound can be increased, and by controlling the particle size of the dispersed phase, the residence properties in blood, the vasopermeability (permeability to blood vessel) and the transmigration properties to inflammatory site can be increased. Therefore, the in vivo kinetics and in vivo distribution of the triazole compound can be improved and targeting can be achieved, and thus, a more effective administration of the active ingredient with suppressed or reduced side effect can be realized. Accordingly, the injectable composition of the present invention is useful for treating a fungal infection via intravenous administration.

EXAMPLES

The following reference examples, examples and experimental examples illustrate the present invention in more detail, but by no means limiting the scope of the invention.

In the following examples, as the oil component, soybean oil which is a triglyceride of a fatty acid having long size chain (a product of Wako Pure Chemicals, Co., Ltd., Japan), a triglyceride of a fatty acid having a medium-size chain [e.g. a tri(capric acid/caprylic acid) glyceryl ester such as "Migriol 812" (trade name, manufactured by Huls Co., Ltd.; hereinafter briefly referred to as "Migriol 812"), a glyceryl tricaprylate such as "Panasate 800" (trade name, manufactured by Nippon Yushi Co., Ltd., Japan; hereinafter simply referred to as "Panasate 800") and the like] were used. As the emulsifier, yolk lecithin (a product of Nippon Seika Co., Ltd., Japan, or a product of Asahi Kasei Co., Ltd., Japan), and as the isotonic agent, glycerol (manufactured by Wako Pure Chemicals, Ltd., Japan) were used.

In the examples, the amount of the triazole compound in the product injection was determined by using high performance liquid chromatography method, and the mean particle size of the disperse phase (fat particle) was determined with the use of a particle size measuring apparatus by light scattering method, "Nicomp".

Reference Example 1 [Production of Compound A]

A compound described as the compound 30 in the Example 27 of EP-A1-0567982, namely the Compound A, was prepared according to the manner as described in the EP-A1-0567982.

Reference Example 2 [Production of Compound B]
Step 1

(1) In 600 ml of ethanol were dissolved 82 g of 2-(2,4-difluorophenyl)-2-[(1R)-1-(3,4,5,6-tetrahydro-2H-pyran-2-yl)oxyethyl]oxirane (prepared by a method disclosed in Japanese Patent Application Laid-open No. 74168/1992, JP-A-4-74168) and 6.3 g of pyridinium p-toluenesulfonate, and the solution was stirred at 55° C. for 1 hour. The reaction mixture was concentrated under reduced pressure. The residue was dissolved in 1 liter of ethyl acetate, and washed twice, each time with 200 ml of water. The aqueous phase was extracted twice, each time with 100 ml of ethyl acetate. The organic phases were collected, washed with saturated aqueous solution of sodium chloride, dried over magnesium sulfate and the solvent was distilled off under reduced pressure. The residue was purified with using silica gel chromatography (gradient eluent; hexane:ethyl acetate= 10:1→8:1→3:1) to give 31.5 g of (1R)-1-[2-(2,4-difluorophenyl)-2-oxiranyl]ethanol as a pale yellow oil.

$^1$H-NMR (CDCl$_3$) δ: 1.14–1.23 (3H, m), 1.77, 2.22 (1H), 2.80, 2.92 (1H), 3.27–3.32 (1H), 4.00–4.20 (1H, m), 6.75–6.94 (2H, m), 7.36–7.48 (1H, m)

(2) (1R)-1-[2-(2,4-difluorophenyl)-2-oxiranyl]ethanol (31.5 g) and 40 g of 3,5-dinitrobenzoyl chloride were dissolved in 500 ml of methylene chloride and, under ice-cooling, 24.1 ml of triethylamine was added dropwise thereinto. After the reaction mixture was stirred at room temperature for 3.5 hours, the resultant mixture was washed successively with 150 ml of water and with 150 ml of 5% aqueous solution of sodium bicarbonate. The resultant was dried over magnesium sulfate and concentrated under reduced pressure. The precipitated crystals were collected by filtration and washed with methylene chloride. The mother liquor and the washing were collected and the solvent was distilled off under reduced pressure. To the residue were added 25 ml of ethyl acetate and 300 ml of methanol, and the mixture was cooled with ice. The precipitated crystals were collected by filtration and recrystallized from a mixture of 25 ml of ethyl acetate and 250 ml of methanol to give 28.7 g of [(1R)-1-[(2R)-2-(2,4-difluorophenyl)-2-oxiranyl]ethyl]3,5-dinitrobenzoate as colorless needles.

m.p. 104°–107° C. (recrystallized from a mixture of ethyl acetate-hexane)

$^1$H-NMR (CDCl$_3$) δ: 1.46 (3H, dd, J=6.6 Hz, J=1.2 Hz), 3.01 (1H, d, J=4.6 Hz), 3.23 (1H, d, J=4.6 Hz), 5.33 (1H, q, J=6.6 Hz), 6.85–7.07 (2H, m), 7.54 (1H, m), 9.13 (2H, d, J=2.2 Hz), 9.25 (1H, t, J=2.2 Hz)

(3) In 2 liter of methanol was dissolved 50 g of [(1R)-1-[(2R)-2-(2,4-difluorophenyl)-2-oxiranyl]ethyl] 3,5-dinitrobenzoate and, at room temperature, 255 ml of 1N aqueous solution of sodium hydroxide was added dropwise to the solution. The reaction mixture was stirred at room temperature for 1 hour, neutralized with 127 ml of 1N aqueous solution of hydrochloric acid and removed off methanol under reduced pressure. To the residue were added 1 liter of ethyl acetate and 200 ml of water. The resultant mixture was extracted with ethyl acetate, and the organic phase was washed with 200 ml of a saturated aqueous solution of sodium chloride, dried over magnesium sulfate and distilled off the solvent under reduced pressure. The residue was purified by silica gel chromatography (eluent; ethyl acetate:hexane=1:3) to give 25 g of (1R)-1-[(2R)-2-(2,4-difluorophenyl)-2-oxiranyl]ethanol as a pale yellow oily substance.

$^1$H-NMR (CDCl$_3$) δ: 1.17 (3H, dd, J=6.6 Hz, 1.2 Hz), 2.05 (1H, br), 2.80 (1H, d, J=5.2 Hz), 3.30 (1H, d, J=5.2 Hz), 4.01–4.17 (1H, m), 6.75–6.93 (2H, m), 7.36–7.48 (1H, m)

(4) To a solution of 16.1 g of (1R)-1-[(2R)-2-(2,4-difluorophenyl)-2-oxiranyl]ethanol in 320 ml of tetrahydrofuran were added, under ice-cooling, 63.3 of triphenylphosphine, 29.5 g of benzoic acid and 42.0 g of diethyl azodicarboxylate, and the mixture was stirred in an argon atmosphere at room temperature for 6 hours. To the reaction mixture were added 800 ml of ethyl acetate and 500 ml of water to fractionate and the aqueous phase was extracted with 200 ml of ethyl acetate. The organic phases were collected, washed successively with water and with a saturated aqueous solution of sodium chloride, dried over magnesium sulfate and concentrated. The residue was purified by using silica gel chromatography (gradient eluent;

hexane:ethyl acetate=15:1→7:1) to give 19.2 g of [(1S)-1-[(2R)-2-(2,4-difluorophenyl)-2-oxiranyl]ethyl]benzoate as a colorless oil.

$^1$H-NMR (CDCl$_3$) δ: 1.37 (3H, d, J=6.6Hz), 2.90 (1H, d, J=5.2 Hz), 3.28 (1H, d, J=5.2 Hz), 5.36 (1H, q, J=6.6 Hz), 6.74–6.94 (2H, m), 7.38–7.60 (4H, m), 7.94–8.01 (2H, m)

IR $v_{max}^{neat}$ (cm$^{-1}$) : 1725, 1615, 1600, 1505, 1450, 1425

(5) In 800 ml of methanol was dissolved 15.9 g of [(1S)-1-[(2R)-2-(2,4-difluorophenyl)-2-oxiranyl]ethyl]benzoate. To the solution was added 28% methanolic solution (12.9 ml) of sodium methylate with ice cooling and the reaction mixture was stirred at room temperature for 6 hours. To the reaction mixture was added 63.2 ml of 1N aqueous solution of hydrochloric acid and the solvent was distilled off under reduced pressure. The residue was purified by silica gel chromatography (gradient eluent; hexane:ethyl acetate=6:1→2:1) to give 9.7 g of (1S)-1-[(2R)-2-(2,4-difluorophenyl)-2-oxiranyl]ethanol as a colorless oil.

$^1$H-NMR (CDCl$_3$) δ: 1.20 (3H, dd, J=6.4 Hz, 2.2 Hz), 2.24 (1H, d, J=1 Hz), 2.92 (1H, d, J=5 Hz), 3.28 (1H, d, J=5 Hz), 4.12 (1H, q, J=6.4 Hz), 6.77–6.95 (2H, m), 7.34 (1H, m)

IR $v_{max}^{neat}$ (cm$^{-1}$): 3420, 2980, 1615, 1600, 1500, 1425

Step 2

(1) 4-(2,2,3,3-tetrafluoropropoxy)aniline (25 g) and pyridine (25.2 g) were dissolved in 200 ml of dichloromethane and, under ice-cooling, 33.3 g of phenyl chloroformate was added dropwise to the solution. After stirring under ice-cooling for 30 minutes, the reaction mixture was washed with water, dried and the solvent was distilled off to give a mixture of phenyl 4-(2,2,3,3-tetrafluoropropoxy)phenylcarbamate and pyridine. To the mixture was added 30.7 g of 2-(diethoxy)ethylamine, and the resultant mixture was stirred at room temperature. The precipitated crystals were collected by filtration and washed with petroleum ether to give 37.8 g of N-(2,2-diethoxyethyl)-N'-[4-(2,2,3,3-tetrafluoropropoxy)phenyl] urea as colorless crystals.

N-(2,2-Diethoxyethyl)-N'-[4-(2,2,3,3-tetrafluoropropoxy)phenyl] urea (37.5 g) was dissolved in a mixture of 560 ml of methanol and 280 ml of water. To the solution was added 300 ml of an aqueous solution containing 0.48M of hydrochloric acid and the mixture was stirred at room temperature for 3 days. The reaction mixture was concentrated under reduced pressure and the precipitated crystals were washed with a mixture of water-methanol (5:1) to give 22.8 g of 1-[4-(2,2,3,3-tetrafluoropropoxy)phenyl]-2-(1H,3H)-imidazolone as colorless powder.

m.p.: 157°–159° C.

(2) To a solution of 10 ml of acetic acid and 2.0 g of 1-[4-(2,2,3,3-tetrafluoropropoxy)phenyl]-2-(1H,3H)-imidazolone was added 0.5 g of 10% palladium-carbon. The mixture was stirred in a hydrogen atmosphere for 7.5 hours. The catalyst was separated by filtration, washed with acetic acid and the filtrate and the washing were collected, followed by distilling off the solvent under reduced pressure. To the residue were added 40 ml of water and 40 ml of ethyl acetate to fractionate, and the ethyl acetate phase was dried over magnesium sulfate and the solvent was distilled off under reduced pressure. to give colorless crystals. The obtained colorless crystals were washed with diisopropyl ether to give 1.86 g of 1-[4-(2,2,3,3-tetrafluoropropoxy) phenyl]-2-imidazolidinone as colorless crystals.

m.p.: 180°–181° C.

$^1$H-NMR (CDCl$_3$) δ: 3.53–3.61 (2H, m), 3.87–3.95 (2H, m), 4.32 (2H, tt, J=11.8 Hz, 1.6 Hz), 4.97 (1H, brs), 6.06 (1H, tt, J=53 Hz, 5.0 Hz), 6.91 (2H, d, J=9.2 Hz), 7.47 (2H, d, J=9.2 Hz)

IR (KBr) $v_{max}$ (cm$^{-1}$): 3250, 1705, 1680, 1515, 1485

Elemental Analysis for C$_{12}$H$_{12}$F$_4$N$_2$O$_2$ Calcd.(%): C 49.32; H 4.14; N 9.59 Found (%): C 49.24; H 3.96; N 9.59

Step 3

To a solution of 1.36 g of (1S)-1-[(2R)-2-(2,4-difluorophenyl)-2-oxiranyl]ethanol obtained in the Step 1 in 30 ml of dichloromethane was added 1.31 ml of diisopropylethylamine at –60° C. in a nitrogen atmosphere, then 1.26 ml of trifluoromethanesulfonic acid anhydride was added dropwise to the mixture over 3 minutes. The resultant mixture was stirred at –60° C. for 20 minutes, successively at –20° C. for 20 minutes. The reaction mixture was subjected to flash chromatography using silica gel (27 g) and eluted with 220 ml of a mixture of dichloromethane-hexane (1:1). The fraction containing the objective compound was concentrated to about 9 ml and the concentrate was added to a mixture of 1.15 g of 1-[4-(2,2,3,3-tetrafluoropropoxy) phenyl]-2-imidazolidinone obtained in Step 2, 18 ml of dimethylformamide and 0.20 g of 60% sodium hydride in oil at –10° C. The resultant mixture was stirred for 20 minutes, and then at 0° C. for further 20 minutes. To the reaction mixture was added 20 ml of water, and the mixture was extracted with 100 ml of ethyl acetate. The ethyl acetate phase was washed with 20 ml of a saturated aqueous solution of sodium chloride, dried over anhydrous magnesium sulfate and the solvent was distilled off under reduced pressure. The residue was purified by silica gel column chromatography (eluent: hexane:ethyl acetate=2:1) to give 1.25 g of 1-[(1R,2S)-2-(2,4-difluorophenyl)-2,3-epoxy-1-methylpropyl]-3-[4-(2,2,3,3-tetrafluoropropoxy)phenyl]-2-imidazolidinone as a colorless powder.

$^1$H-NMR (CDCl$_3$) δ: 1.21 (3H, d, J=7.2 Hz), 2.75 (1H, d, J=7.0 Hz), 3.15 (1H, d, J=7.0 Hz), 3.42–3.64 (2H, m), 3.71–3.81 (2H, m), 4.32 (2H, tt, J=12 Hz, 1.4 Hz), 4.80 (1H, q, J=7.2 Hz), 6.06 (1H, tt, J=53 Hz, 5 Hz), 6.76–6.9 (2H, m), 6.91 (2H, d, J=9.2 Hz), 7.35–7.5 (1H, m), 7.48 (2H, d, J=9.2 Hz)

Step 4

A mixture of 0.41 g of 1H-1,2,4-triazole, 0.19 g of 60% sodium hydride in oil and 12 ml of dimethylformamide was stirred at room temperature for 20 minutes, and added with 0.85 g of 1-[(1R,2S)-2-(2,4-difluorophenyl)-2,3-epoxy-1-methylpropyl]-3-[4-(2,2,3,3-tetrafluoropropoxy)phenyl]-2-imidazolidinone obtained in Step 3 and the resultant mixture was heated at 60° C. for 4 hours. After cooling, 20 ml of water was added to the reaction mixture and the mixture was extracted with 80 ml of ethyl acetate. The extract was washed with 20 ml of a saturated aqueous solution of sodium chloride, dried over anhydrous magnesium sulfate and concentrated under reduced pressure. The residue was purified by silica gel chromatography (gradient eluent: hexane:ethyl acetate=1:2→1:5) to give 1-[(1R,2R)-2-(2,4-difluorophenyl)-2-hydroxy-1-methyl-3-(1H-1,2,4-triazol-1-yl)propyl]-3-[4-(2,2,3,3-tetrafluoropropoxy) phenyl]-2-imidazolidinone (Compound B) as a colorless powder.

$^1$H-NMR (CDCl$_3$) δ: 1.06 (3H, d, J=7.0 Hz), 3.66–3.73 (1H, m), 3.80–3.95 (3H, m), 4.33 (2H, tt, J=12 Hz, 1.6 Hz), 4.52 (1H, d, J=14.4 Hz), 4.5–4.65 (1H, m), 5.08 (1H, d, J=14.4 Hz), 5.45–5.65 (1H, br), 6.06 (1H, tt, J=53 Hz, 4.8 Hz), 6.70–6.83 (2H, m), 6.94 (2H, d, J=9.2 Hz), 7.39–7.54 (1H, m), 7.50 (2H, d, J=9.2 Hz), 7.74 (1H, s), 7.88 (1H, s)

Elemental Analysis for C$_{24}$H$_{23}$F$_6$N$_5$O$_3$ Calcd.(%): C 53.04; H 4.27; N 12 89 Found (%): C 53.04; H 4.50; N 12.82

IR (KBr) $v_{max}$ (cm$^{-1}$): 3380, 1690, 1665, 1510, 1485, 1440

Reference Example 3 [Production of Compound C]

(1) By using 4-(1,1,2,2-tetrafluoroethoxy)aniline instead of 4-(2,2,3,3-tetrafluoropropoxy)aniline as the starting compound in Step 2-(1) of the Reference Example 2, 1-[4-(1,1,2,2-tetrafluoroethoxy)phenyl]-2-(1H,3H)-imidazolone was obtained.

m.p.: 161°–163° C.

(2) 1-[4-(1,1,2,2-tetrafluoroethoxy)phenyl]-2-imidazolidinone was obtained in the same manner as in Step 2-(2) of Reference Example 2 except for using 1-[4-(1,1,2,2-tetrafluoroethoxy)phenyl-2-(1H,3H)-imidazolone instead of 1-[4-(2,2,3,3-tetrafluoropropoxy)phenyl]-2-(1H,3H)-imidazolone.

m.p.: 169°–171° C.

(3) The procedures of Step 3 of Reference Example 2 were repeated except for using 1-[4-(1,1,2,2-tetrafluoroethoxy)phenyl]-2-imidazolidinone instead of 1-[4-(2,2,3,3-tetrafluoropropoxy) phenyl]-2-imidazolidinone to give 1-[(1R,2S)-2-(2,4-difluorophenyl)-2,3-epoxy-1-methylpropyl]-3-[4-(1,1,2,2-tetrafluoroethoxy)phenyl]-2-imidazolidinone as a colorless powder.

$^1$H-NMR (CDCl$_3$) δ: 1.22 (3H, d, J=7.4 Hz), 2.75 (1H, d, J=5 Hz), 3.14 (1H, d, J=5 Hz), 3.44–3.65 (2H, m), 3.73–3.84 (2H, m), 4.80 (1H, q, J=7.4 Hz), 5.89 (1H, tt, J=53 Hz, 2.8 Hz), 6.77–6.93 (2H, m), 7.17 (2H, d, J=9 Hz), 7.34–7.46 (1H, m), 7.55 (2H, d, J=9 Hz)

IR (KBr) $v_{max}$ (cm$^{-1}$): 1680, 1615, 1510, 1485, 1425

(4) 1-(1R,2R)-2-(2,4-difluorophenyl)-2-hydroxy-1-methyl-3-(1H-1,2,4-triazol-1-yl)propyl]-3-[4-(1,1,2,2-tetrafluoroethoxy)phenyl]-2-imidazolidinone (the Compound C) was obtained as a colorless powder in the same manner as in Step 4 of Reference Example 2 except that 1-[(1R,2S)-2-(2,4-difluorophenyl)-2,3-epoxy-1-methylpropyl]-3-[4-(1,1,2,2-tetrafluoroethoxy)phenyl]-2-imidazolidinone was used instead of 1-[(1R,2S)-2-(2,4-difluorophenyl)-2,3-epoxy-1-methylpropyl]-3-[4-(2,2,3,3-tetrafluoropropoxy)phenyl]-2-imidazolidinone.

$^1$H-NMR (CDCl$_3$) δ: 1.07 (3H, d, J=7 Hz), 3.67–3.75 (1H, m), 3.82–4.01 (3H, m), 4.50 (1H, d, J=15 Hz), 4.65 (1H, m), 5.10 (1H, d, J=15 Hz), 5.3–5.6 (1H, br), 5.91 (1H, tt, J=53 Hz, 3.0 Hz), 6.72–6.83 (2H, m), 7.21 (2H, d, J=9.2 Hz), 7.36–7.49 (1H, m), 7.58 (2H, d, J=9.2 Hz), 7.75 (1H, s), 7.86 (1H, s)

Elemental Analysis for C$_{23}$H$_{21}$F$_6$N$_5$O$_3$ Calcd. (%) C 52.18; H 4.00; N 13.23 Found (%): C 52.30; H 3.95; N 13.28

IR (KBr) $v_{max}$ (cm$^{-1}$) : 3380, 1680, 1615, 1510, 1480, 1425

Reference Example 4 [Production of Compound D]

(1) By using 2-(2-fluorophenyl)-2-[(1R)-1-(3,4,5,6-tetrahydro-2H-pyran-2-yl)oxyethyl]oxirane (prepared by a method described in EP-A-0548553) instead of 2-(2,4-difluorophenyl)-2-[(1R)-1-(3,4,5,6-tetrahydro-2H-pyran-2-yl)oxyethyl]oxirane, [(1R)-1-[(2R)-2-(2-fluorophenyl)-2-oxiranyl]ethyl] 3,5-dinitrobezoate was obtained in the similar manner as in Step 1-(1) and -(2) of Reference Example 2.

Colorless prisms (crystallized from ethyl acetate)

m.p. 183°–184° C.

$^1$H-NMR (CDCl$_3$) δ: 1.47 (3H, dd, J=6.6 Hz, 1.6 Hz), 3.03 (1H, d, J=4.7 Hz), 3.23 (1H, d, J=4.7 Hz), 5.35 (1H, q, J=6.6 Hz), 7.09–7.59 (4H, m), 9.13 (2H, d, J=2.2 Hz), 9.23 (1H, t, J=2.2 Hz)

[α]$^{23}_D$24.7° (c=1.0, in CHCl$_3$)

Elemental Analysis for C$_{17}$H$_{13}$FN$_2$O$_7$ Calcd.(%): C 54.26; H 3.48; N 7.44 Found (%): C 54.23; H 3.25; N 7.41

(2) The procedures of Step 1-(3) of Reference Example 2 were repeated except for using [(1R)-1-[(2R)-2-(2-fluorophenyl)-2-oxiranyl]ethyl] 3,5-dinitrobezoate instead of [(1R)-1-[(2R)-2-(2,4-difluorophenyl)-2-oxiranyl]ethyl] 3,5-dinitrobezoate to give (1R)-1-[(2R)-2-(2-fluorophenyl)-2-oxiranyl]ethanol as a colorless oil.

$^1$H-NMR (CDCl$_3$) δ: 1.17 (3H, dd, J=6.6 Hz, 1.0 Hz), 1.78 (1H, d, J=8.2 Hz), 2.81 (1H, d, J=5.3 Hz), 3.32 (1H, d, J=5.3 Hz), 4.15 (1H, m), 6.99–7.47 (4H, m) (3) By using (1R)-1-[(2R)-2-(2-fluorophenyl)-2-oxiranyl]ethanol instead of (1R)-1-[(2R)-2-(2,4-difluorophenyl)-2-oxiranyl]ethanol, (1S)-1-[(2R)-2-(2-fluorophenyl)-2-oxiranyl]ethanol was obtained in the same manner as in Step 1-(4) and -(5) of Reference Example 2.

Colorless oil $^1$H-NMR (CDCl$_3$) δ: 1.21 (3H, d, J=7 Hz), 2.27 (1H, d, J=2 Hz), 2.96 (1H, d, J=5 Hz), 3.30 (1H, d, J=5 Hz), 4.16 (1H, dd, J=7 Hz, 2 Hz), 7.03–7.44 (4H, m)

(4) 1-[(1R,2S)-2,3-epoxy-2-(2-fluorophenyl)-1-methylpropyl]-3-[4-(1,1,2,2-tetrafluoroethoxy)phenyl]-2-imidazolidinone was obtained in the same manner as in Step 3 of Reference Example 2, except that (1S)-1-[(2R)-2-(2-fluorophenyl)-2-oxiranyl]ethanol obtained in above Step (3) was used instead of (1S)-1-[(2R)-2-(2,4-difluorophenyl)-2-oxiranyl]ethanol, and that 1-[4-(1,1,2,2-tetrafluoroethoxy)phenyl]-2-imidazolidinone obtained in Step (2) of Reference Example 3 was used instead of 1-[4-(2,2,3,3-tetrafluoropropoxy) phenyl]-2-imidazolidinone.

Colorless powder (crystallized from diisopropyl ether).

m.p.: 148°–149° C.

$^1$H-NMR (CDCl$_3$) δ: 1.24 (3H, d, J=7.2 Hz) , 2.78 (1H, d, J=5.0 Hz), 3.15 (1H, d, J=5.0 Hz), 3.45–3.84 (4H, m), 4.85 (1H, q, J=7.2 Hz), 5.90 (1H, tt, J=53.2 Hz, 2.8 Hz), 7.02–7.60 (8H, m)

Elemental Analysis for C$_{21}$H$_{19}$F$_5$N$_2$O$_3$ Calcd.(%): C 57.02; H 4.33; N 6.33 Found (%): C 56.90; H 4.36; N 6.31

(5) 1-(1R,2R)-2-(2-fluorophenyl)-2-hydroxy-1-methyl-3-(1H-1,2,3-triazol-1-yl)propyl]-3-[4-(1,1,2,2-tetrafluoroethoxy)phenyl]-2-imidazolidinone (the Compound D) was obtained in the similar manner as in Step 4 of Reference Example 2 except for using 1-[(1R,2S)-2,3-epoxy-2-(2-fluorophenyl)-1-methylpropyl]-3-[4-(1,1,2,2-tetrafluoroethoxy)phenyl]-2-imidazolidinone instead of 1-[(1R,2S)-2-(2,4-difluorophenyl)-2,3-epoxy-1-methylpropyl]-3-[4-(2,2,3,3-tetrafluoropropoxy)phenyl]-2-imidazolidinone.

Colorless needles $^1$H-NMR (CDCl$_3$) δ: 1.06 (3H, d, J=7.0 Hz), 3.68–4.05 (4H, m), 4.51 (1H, d, J=14.4 Hz), 4.65–4.80 (1H, m), 5.15 (1H, d, J=14.4 Hz), 5.25 (1H, br), 5.91 (1H, tt, J=53.2 Hz, 3 Hz), 6.95–7.63 (8H, m), 7.74 (1H, s), 7.82 (1H, s)

Elemental Analysis for C$_{23}$H$_{22}$F$_5$N$_5$O$_3$ Calcd.(%): C 54.01; H 4.34; N 13.69 Found (%): C 53.96; H 4.48; N 13.69

Reference Example 5 [Production of Compound E]

(1) The procedures of Step 3 of Reference Example 2 were repeated except for using (1S)-1-[(2R)-2-(2-fluorophenyl)-2-oxiranyl]ethanol obtained in above Step (3) of Reference Example 4 instead of (1S)-1-[(2R)-2-(2,4-difluorophenyl)-2-oxiranyl]ethanol to give 1-[(1R,2S)-2,3-epoxy-2-(2-fluorophenyl)-1-methylpropyl]-3-[4-(2,2,3,3-tetrafluoropropoxy)phenyl]-2-imidazolidinone.

Colorless powder (crystallized from diisopropyl ether)

m.p.: 144°–145° C.

$^1$H-NMR (CDCl$_3$) δ: 1.22 (3H, d, J=7.4 Hz), 2.77 (1H, d, J=5.0 Hz), 3.16 (1H, d, J=5.0 Hz), 3.47–3.77 (4H, m), 4.32

(2H, tt, J=12 Hz, 1.6 Hz), 4.85 (1H, q, J=7.4 Hz), 6.07 (1H, tt, J=53 Hz, 5 Hz), 6.89–7.52 (8H, m)

Elemental Analysis for $C_{22}H_{21}F_5N_2O_3$ Calcd.(%): C 57.90; H 4.64; N 6.14 Found (%): C 57.94; H 4.60; N 6.19

(2) By using 1-[(1R,2S)-2,3-epoxy-2-(2-fluorophenyl)-1-methylpropyl]-3-[4-(2,2,3,3-tetrafluoropropoxy)phenyl]-2-imidazolidinone obtained in the above Step (1) instead of 1-[(1R,2S)-2,3-epoxy-2-(2,4-difluorophenyl)-1-methylpropyl]-3-[4-(2,2,3,3-tetrafluoroprophenyl)phenyl]-2-imidazolidinone, 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy) phenyl]-2-imidazolidinone (Compound E) was obtained as a colorless powder in the same manner as in Step 4 of Reference Example 2.

$^1$H-NMR (CDCl$_3$) δ: 1.06 (3H, d, J=7.0 Hz), 3.66–4.05 (4H, m), 4.33 (2H, tt, J=12 Hz, 1.6 Hz), 4.52 (1H, d, J=14 Hz), 4.60–4.77 (1H, m), 5.13 (1H, d, J=14 Hz), 5.35 (1H, br), 6.07 (1H, tt, J=53 Hz, 5 Hz), 6.91–7.53 (8H, m), 7.73 (1H, s), 7.83 (1H, s)

Elemental Analysis for $C_{24}H_{24}F_5N_5O_3$ Calcd.(%): C 54.86; H 4.60; N 13.33 Found (%): C 54.66; H 4.57; N 13.26

Example 1

To 10 g of soybean oil was added 0.1 g of Compound A under heating to disperse or dissolve Compound A. Purified yolk lecithin (0.24 g; manufactured by Nippon Seika Co., Ltd., Japan) and glycerol (2.5 g) were added to the mixture and resultant mixture was vigorously stirred under heating to dissolve. To the resulting solution was added a suitable amount of distilled water and the mixture was stirred with using a Polytron-homogenizer to give a roughly emulsified emulsion (rough emulsion). After subjecting the rough emulsion to further emulsification with the use of a Microfluidizer, the emulsion was added with distilled water up to 100 ml, filtrated with a filter having a pore size of 0.45 μm to give an injectable composition (injection) containing Compound A in a proportion of 297 μg/ml and dispersed fat particles having a mean particle size of 764 nm.

Example 2

An injection containing 636 μg/ml of Compound A and fat particles, dispersed in water, having a mean particle size of 133 nm was prepared in the same manner as in Example 1 except for using 10 g of the soybean oil, 0.1 g of Compound A, 1.2 g of the purified yolk lecithin and 2.5 g of glycerol.

Example 3

By using 10 g of the soybean oil, 0.1 g of Compound A, 6.0 g of the purified yolk lecithin and 2.5 g of glycerol, an injection containing 812 μg/ml of Compound A and dispersed fat particles having a mean particle size of 56 nm was obtained in the similar manner as in Example 1.

Example 4

An injection containing 1,166 μg/ml of Compound A and fat particles, dispersed in water, having a mean or average particle size of 59 nm was prepared in the similar manner as in Example 1, except that 20 g of the soybean oil, 0.2 g of Compound A, 6.0 g of purified yolk lecithin and 2.5 g of glycerol were used.

Example 5

The procedures of Example 1 were repeated except for using 10 g of the soybean oil, 0.1 g of Compound A, 10 g of the purified yolk lecithin and 2.5 g of glycerol to give an injection containing 820 μg/ml of Compound A and dispersed fat particles having a mean particle size of 45 nm.

Example 6

An injection containing 32 μg/ml of Compound A and dispersed fat particles having a mean particle size of 75 nm was obtained according to the same manner as in Example 1, except that 5 g of the soybean oil, 0.005 g of Compound A, 1.2 g of the purified yolk lecithin and 2.5 g of glycerol were employed.

Example 7

By using 10 g of the soybean oil, 0.01 g of Compound A, 1.2 g of the purified yolk lecithin and 2.5 g of glycerol, an injectable composition containing 70 μg/ml of Compound A and dispersed fat particles having a mean particle size of 110 nm was prepared according to the similar manner as in Example 1.

Example 8

The procedures of Example 1 were repeated except that 20 g of the soybean oil, 0.02 g of Compound A, 1.2 g of the purified yolk lecithin and 2.5 g of glycerol were used to obtain an injection containing 154 μg/ml of compound A and dispersed fat particles having a mean particle size of 163 nm.

Example 9

An injectable composition containing 394 μg/ml of Compound A and fat particles, dispersed in water, having a mean particle size of 101 nm was obtained in the same manner as in Example 1 except for using 10 g of the soybean oil, 0.05 g of Compound A, 1.2 g of the purified yolk lecithin and 2.5 g of glycerol.

Example 10

An injection containing 509 μg/ml of Compound A, and dispersed fat particles having a mean or average particle size of 39 nm was prepared by using 5 g of "Migriol 812", 0.05 g of Compound A, 2.4 g of the purified yolk lecithin and 2.5 g of glycerol in the similar manner as in Example 1.

Example 11

An injectable composition containing 500 μg/ml of itraconazole and dispersed fat particles of a mean particle size of 110 nm was obtained in the same manner as in Example 1, except that 10 g of the soybean oil, 0.1 g of itraconazole, 1.2 g of the purified yolk lecithin and 2.5 g of glycerol were employed.

Example 12

By using 10 g of the soybean oil, 0.1 g of saperconazole, 1.2 g of the purified yolk lecithin and 2.5 g of glycerol, an injection containing 500 μg/ml of saperconazole and fat particles, dispersed in water, having a mean particle size of 110 nm was obtained in the similar manner as in Example 1.

Example 13

The procedures of Example 1 were repeated except that 10 g of the soybean oil, 0.1 g of D0870, 1.2 g of the purified yolk lecithin and 2.5 g of glycerol were used to obtain an injectable composition containing 500 μg/ml of D0870 and dispersed fat particles having a mean particle size of 110 nm.

Experimental Example 1

The injectable emulsion composition containing Compound A obtained in Example 4 was intravenously administered to a rat, and the time-dependent level (concentration) of Compound A in blood was determined with the lapse of time. As a control, an injection wherein Compound A was solubilized by including with 10% cyclodextrin, was employed. The results are shown in FIG. 1.

As apparent from FIG. 1, according to the injectable oil-in-water emulsion composition of the present invention, higher level of the drug concentration can be obtained at early stage of the administration than that of the solubilized injection containing the clathrate of the drug with cyclodextrin.

Experimental Example 2

Figure 2:
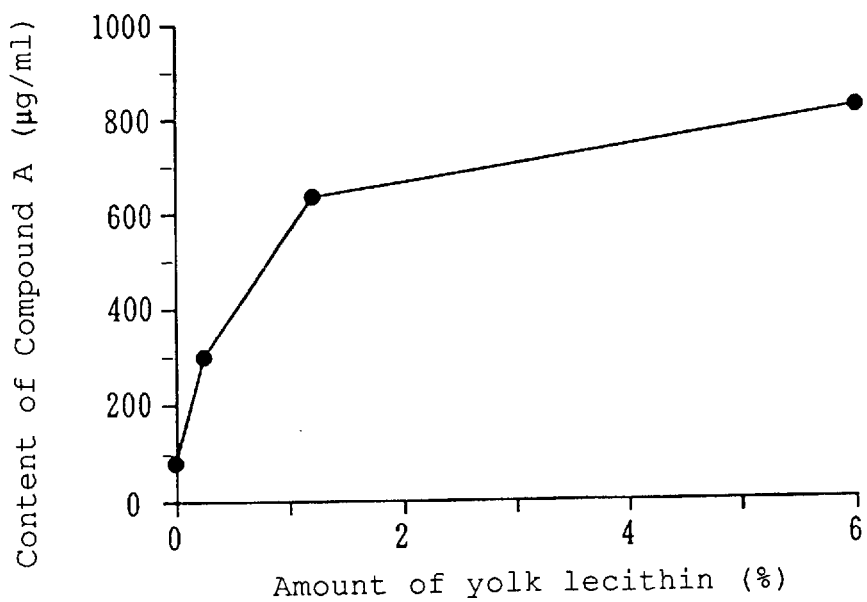
FIG. 2 is a graph showing the relationship between the amount of the yolk lecithin and the content of Compound A in Experimental Example 2.

The relationship between the proportion of Compound A and the amount of the yolk lecithin was determined by using the injections obtained in Examples 1 to 3. As a control, an injection which was not added with the yolk lecithin was employed. The results are set forth in FIG. 2. From the results in FIG. 2, it is shown that the concentration of Compound A increases with an increasing amount of the yolk lecithin added thereto. Since the solubility of Compound A in the soybean oil is about 0.9 mg/ml, provided that the compound distributes only in the oil component, the concentration of Compound A based on the whole composition should be about 90 µg/ml regardless of the amount of the lecithin. Therefore, it should be understood that addition of the yolk lecithin can extremely increase the concentration of Compound A in the injection.

Example 14

To 40 g of "Migriol 812" was added 0.4 g of Compound A, and the mixture was dissolved under stirring at 60° C. to give a solution. To the resultant solution, a mixture of 2.4 g of purified yolk lecithin (Asahi Kasei Co., Ltd., Japan), 4.5 g of glycerol and 150 ml of distilled water, which was prepared by mixing under nitrogen atmosphere at 60° C., was added. The resultant mixture was stirred under nitrogen stream for 10 minutes with the use of a Polytron-homogenizer (Kinematica Co., Ltd.) to give a roughly emulsified emulsion (rough emulsion). The rough emulsion was further emulsified by using a high-pressure homogenizer (Nanomizer, a product of Nanomizer Co., Ltd.), under a pressure of 500 kg/ml for one hour. After completion of emulsification, the resultant emulsion was filtrated with a filter having a pore size of 0.45 µm to give an injectable emulsion composition containing 2 mg/ml of Compound A and dispersed fat particles having a mean particle size of 250 nm.

Example 15

The procedures of Example 14 were repeated except for using 40 g of "Migriol 812", 0.4 g of Compound A, 4.0 g of the purified yolk lecithin, 4.5 g of glycerol and 150 ml of distilled water to give an injectable emulsion composition (emulsion injection) containing 2 mg/ml of Compound A and dispersed fat particles having a mean particle size of 130 nm.

Example 16

An injectable emulsion composition containing 2 mg/ml of Compound A and dispersed fat particles having a mean particle size of 68 nm was prepared in the same manner as in Example 14, except that 40 g of "Migriol 812", 0.4 g of Compound A, 12.0 g of the purified yolk lecithin, 4.5 g of glycerol and 150 ml of distilled water were employed.

Example 17

An injectable emulsion composition containing 2 mg/ml of Compound B and dispersed fat particles having a mean particle size of 180 nm was obtained in the same manner as in Example 14, except for using 40 g of "Panasate 800", 0.4 g of Compound B, 2.4 g of the purified yolk lecithin, 4.5 g of glycerol and 150 ml of distilled water.

Example 18

The procedures of Example 14 were repeated except for using 40 g of "Panasate 800", 1 g of Compound B, 2.4 g of the purified yolk lecithin, 4.5 g of glycerol and 150 ml of distilled water to give an injectable emulsion composition containing 5 mg/ml of Compound B and dispersed fat particles having a mean particle size of 180 nm.

Example 19

An injectable emulsion composition containing 2 mg/ml of Compound B and fat particles, dispersed in water, having a mean particle size of 180 nm was obtained in the same manner as in Example 14 except for using 40 g of "Migriol 812", 0.4 g of Compound B, 2.4 g of the purified yolk lecithin, 4.5 g of glycerol and 150 ml of distilled water.

Example 20

By using 40 g of the soybean oil, 0.2 g of Compound B, 2.4 g of the purified yolk lecithin, 4.5 g of glycerol and 150 ml of distilled water, an injectable emulsion composition containing 1 mg/ml of Compound B and dispersed fat particles having a mean particle size of 180 nm was obtained in the similar manner as in Example 14.

Example 21

An injectable emulsion composition containing 2 mg/ml of Compound B and dispersed fat particles having a mean particle size of 133 nm was prepared in the similar manner as in Example 14, except that 40 g of "Migriol 812", 0.4 g of Compound B, 4 g of the purified yolk lecithin, 4.5 g of glycerol and 150 ml of distilled water were employed.

Example 22

The procedures of Example 14 were repeated to give an injectable emulsion composition containing 2 mg/ml of Compound C and dispersed fat particles having a mean particle size of 180 nm, by using 40 g of "Panasate 800", 0.4 g of Compound C, 2.4 g of the purified yolk lecithin, 4.5 g of glycerol and 150 ml of distilled water in the same manner as in Example 14.

Example 23

An injectable emulsion composition containing 2 mg/ml of Compound D and dispersed fat particles having a mean particle size of 180 nm was obtained in the same manner as in Example 14, except for using 40 g of "Panasate 800", 0.4 g of Compound D, 2.4 g of the purified yolk lecithin, 4.5 g of glycerol and 150 ml of distilled water.

Example 24

By using 40 g of "Panasate 800", 0.4 g of Compound E, 2.4 g of the purified yolk lecithin, 4.5 g of glycerol and 150 ml of distilled water, an injectable emulsion composition containing 2 mg/ml of Compound E and dispersed fat particles having a mean particle size of 180 nm was obtained in the similar manner as in Example 14.

Example 25

An injectable emulsion composition containing 2-mg/ml of Compound B and dispersed fat particles having a mean particle size of 364 nm was obtained in the same manner as in Example 14 except that 40 g of "Panasate 800", 0.4 g of Compound B, 1.6 g of the purified yolk lecithin, 4.5 g of glycerol and 150 ml of distilled water were used.

Experimental Example 3

By using "Migriol 812" as the oil component, injections differing in the proportion of the purified yolk lecithin were prepared and the content of Compound A was determined in the same manner as in Experimental Example 2. The results are shown in FIG. 3.

Figure 3:
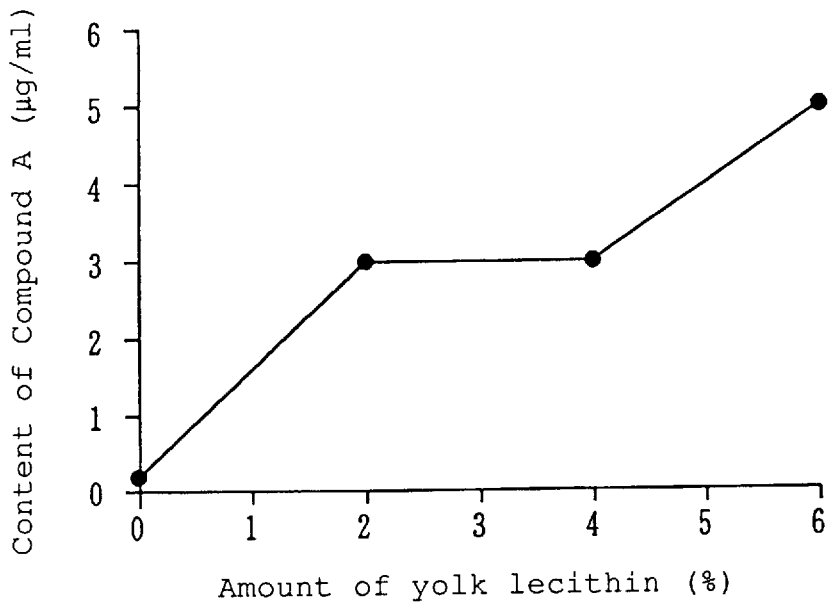
FIG. 3 is a graph illustrating the relationship between the amount of yolk lecithin and the content of Compound A in Experimental Example 3.

As apparent from FIG. 3, the content of Compound A was increased with an increasing amount of the yolk lecithin in the injections containing "Migriol 812", similar to those containing the soybean oil.

Experimental Example 4

Figure 4:
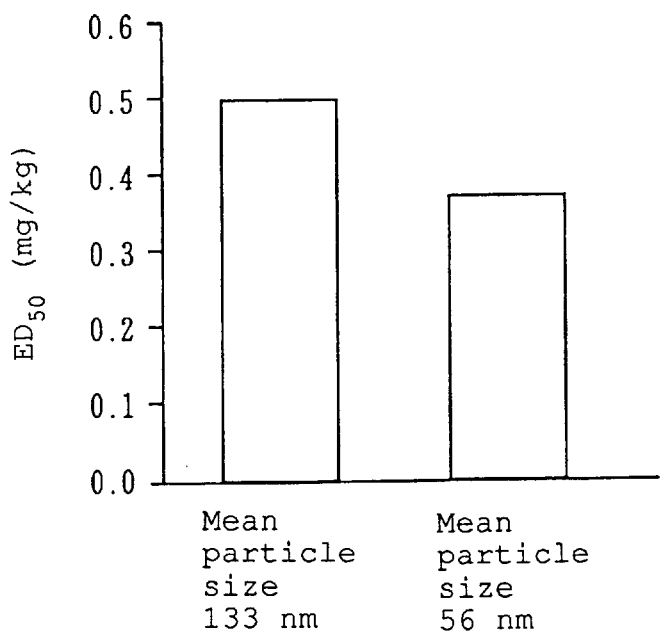
FIG. 4 is a graph showing the relationship between the drug efficacy and the particle size of the injections in Experimental Example 4.

The effect of the particle size on the drug efficacy for a mouse infected with Candida was examined, and the results are illustrated in FIG. 4. As shown in FIG. 4, there was not so much difference on the drug efficacy (effect) between the particle sizes of the injections, and the excellent antifungal activities in vivo were observed both in the injection having a mean particle size of the disperse phase of 133 nm and in the injection having a mean particle size of the disperse phase of 56 nm.

Experimental Example 5

Figure 5:
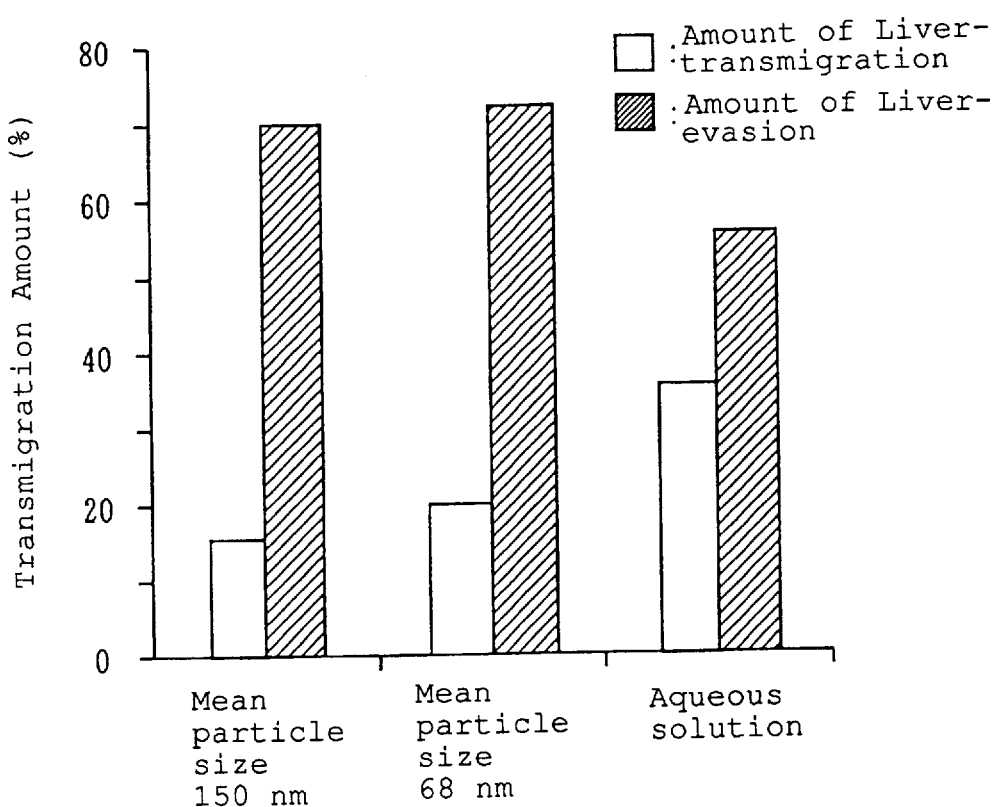
FIG. 5 is a graph illustrating the effect of the particle size of the injection on the evasion against RES in Experimental Example 5.

The effect of the particle size on the evasion against a reticuloendothelial system (RES) such as liver was determined by rat liver-perfusion test. The results are shown in FIG. 5. The results in FIG. 5 shows that, regardless of the particle size of the disperse phase, the liver-evasion in higher level was observed in case administered with the emulsion injection than that administered with an aqueous solution of cyclodextrin.

Experimental Example 6

By treating the injections differing in the average particle size of the disperse phase with using an autoclave at 121° C. for 20 minutes, the effect of the particle size on the stability against autoclave treatment was examined. The results are set forth in Table 1.

TABLE 1

| Injection | Average particle size (nm) | Change of particle size | Change of external appearance |
|---|---|---|---|
| Example 3 | 56 | none | colored, phase separated |
| Example 15 | 130 | none | none |
| Example 17 | 180 | none | none |
| Example 25 | 364 | reduced | none |

As illustrated in Table 1, the injectable emulsion compositions having a mean particle size of the disperse phase of 130 to 180 nm were stable against the autoclave treatment. It was observed that both the emulsion injection having an excessively small mean particle size and the emulsion injection having an excessively large mean particle size have poor stabilities.

We claim:

1. An injectable oil-in-water emulsion composition for intravenous administration which comprises an oil component, an emulsifier and an antifungal triazole compound of the formula (I)

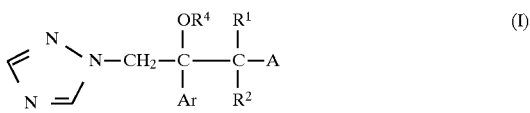

wherein Ar represents a substituted phenyl group; $R^1$ and $R^2$ represent, independently, a hydrogen atom or a lower alkyl group, or $R^1$ and $R^2$ may together form a lower alkylene group; $R^4$ represents a hydrogen atom or an acyl group; and A represents an optionally substituted cyclic amide group bonded through a nitrogen atom, or a salt thereof, wherein said triazole compound is dissolved in said oil-in-water emulsion in a proportion of 0.0001 to 2% (W/V), wherein the oil component of said oil-in-water emulsion is a triglyceride of medium-size chain fatty acids having 6 to 14 carbon atoms, the amount of said oil component being 2 to 25% by weight, and wherein the emulsifier is lecithin, the amount of said emulsifier being 0.5 to 5% (W/V) and the proportion of said emulsifier relative to the total weight of the oil component being 1.0 to 15% by weight.

2. The composition as claimed in claim 1, wherein the compound of the formula (I) is:

2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, 1-[(1R,2R)-2-(2,4-difluorophenyl)-2-hydroxy-1-methyl-3-(1H-1,2,4-triazol-1-yl)propyl]-3-[4-(2,2,3,3-tetrafluoropropoxy)phenyl]-2-imidazolidinone, 1-[(1R,2R)-2-(2,4-difluorophenyl)-2-hydroxy-1-methyl-3-(1H-1,2,4-triazol-1-yl)propyl]-3-[4-(1,1,2,2-tetrafluoroethoxy)phenyl]-2-imidazolidinone, 1-[(1R,2R)-2-(2-fluorophenyl)-2-hydroxy-1-methyl-3-(1H-1,2,4-triazol-1-yl)propyl]-3-[4-(1,1,2,2-tetrafluoroethoxy)phenyl]-2-imidazolidinone, or 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2-imidazolidinone.

3. The composition as claimed in claim 1, wherein said triglyceride is a caprylic/capric triglyceride or a caprylic triglyceride.

4. The composition as claimed in claim 1, wherein a dispersed particle having a mean particle size of 25 to 500 nm is dispersed in water.

5. The composition as claimed in claim 1, wherein the cyclic amide represented by A is a group of the following formula (II) or (IIIa)

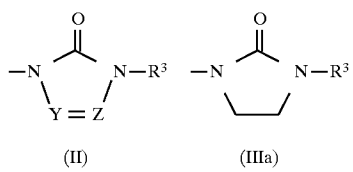

wherein $R^3$ represents a group bonded through a carbon atom; and Y and Z independently represent a nitrogen atom or a methine group which may be substituted with a lower alkyl group.

6. The composition as claimed in claim 5, wherein the substituted phenyl group represented by Ar is a phenyl group substituted with one or two fluorine atoms; $R^1$ and $R^2$ are independently a hydrogen atom or an alkyl group having 1 to 4 carbon atoms; the groups bonded through a carbon atom shown by $R^3$ is an optionally substituted phenyl group; and $R^4$ is a hydrogen atom.

7. The composition as claimed in claim 6, wherein the optionally substituted phenyl group represented by $R^3$ is a halogenated phenyl group, a halogenated $C_{1-6}$ alkyl-phenyl group, or a halogenated $C_{1-6}$ alkoxy-phenyl group.

8. The composition as claimed in claim 5, which contains the triazole compound where the cyclic amide group represented by A is the group of the formula (II), wherein oil particles having a mean particle size of 110 to 250 nm are dispersed in water.

9. The composition as claimed in claim 5, which contains the triazole compound where the cyclic amide group represented by A is the group of the formula (IIIa), wherein oil particles having a mean particle size of 140 to 250 nm are dispersed in water.

10. An injectable oil-in-water emulsion composition for intravenous administration which comprises an oil component and an emulsifier and an antifungal triazole compound of the following formula (IV) dissolved in said disperse phase, wherein said disperse phase has a mean particle size of 30 to 250 nm:

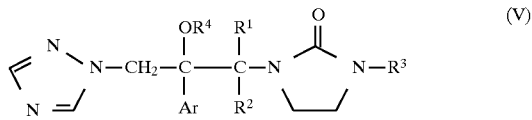

wherein Ar represents a phenyl group substituted with a fluorine atom; $R^1$ and $R^2$ independently represent a hydrogen atom or a methyl group; $R^3$ represents a phenyl group having a $C_{1-6}$ alkoxy group substituted with a fluorine group; $R^4$ represents a hydrogen atom; and Y and Z respectively represent a nitrogen atom or a methine group, wherein said triazole compound is dissolved in said oil-in-water emulsion in a proportion of 0.0001 to 2% (W/V), wherein the oil component of said oil-in-water emulsion is a triglyceride of medium-size chain fatty acids having 6 to 14 carbon atoms, the amount of said oil component being 2 to 25% by weight, and wherein the emulsifier is lecithin, the amount of said emulsifier being 0.5 to 5% (W/V) and the proportion of said emulsifier relative to the total weight of the oil component being 1.0 to 15% by weight.

11. An injectable oil-in-water emulsion composition for intravenous administration which comprises an oil component, an emulsifier, and an antifungal triazole compound of the following formula (V) dissolved in said disperse phase, wherein said disperse phase has a mean particle size of 30 to 250 nm:

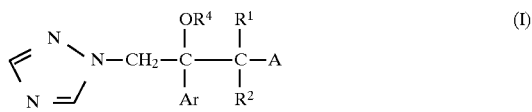

wherein Ar represents a phenyl group substituted with a fluorine atom; $R^1$ and $R^2$ independently represent a hydrogen atom or a methyl group; $R^3$ represents a phenyl group having a $C_{1-6}$ alkoxy group substituted with a fluorine atom; and $R^4$ denotes a hydrogen atom, wherein said triazole compound is dissolved in said oil-in-water emulsion in a proportion of 0.0001 to 2% (W/V), wherein the oil component of said oil-in-water emulsion is a triglyceride of medium-size chain fatty acids having 6 to 14 carbon atoms, the amount of said oil component being 2 to 25% by weight, and wherein the emulsifier is lecithin, the amount of said emulsifier being 0.5 to 5% (W/V) and the proportion of said emulsifier relative to the total weight of the oil component being 1.0 to 15% by weight.

12. A method of producing an injectable oil-in-water emulsion composition for intravenous administration, which comprises dispersing a mixture of (1) a disperse phase containing an oil component and an emulsifier and (2) an antifungal triazole compound of the following formula (I) in water:

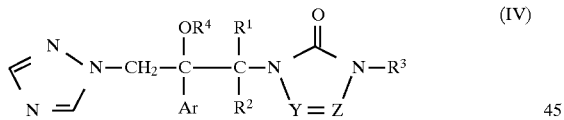

wherein Ar represents a substituted phenyl group; $R^1$ and $R^2$ respectively represent a hydrogen atom or a lower alkyl group, or $R^1$ and $R^2$ may together form a lower alkylene group; $R^4$ represents a hydrogen atom or an acyl group; and A denotes an optionally substituted cyclic amide group bonded through a nitrogen atom, wherein said triazole compound is dissolved in said oil-in-water emulsion in a proportion of 0.0001 to 2% (W/V), wherein the oil component of said oil-in-water emulsion is a triglyceride of medium-size chain fatty acids having 6 to 14 carbon atoms, the amount of said oil component being 2 to 25% by weight, and wherein the emulsifier is lecithin, the amount of said emulsifier being 0.5 to 5% (W/V) and the proportion of said emulsifier relative to the total weight of the oil component being 1.0 to 15% by weight.

13. A method of treating a fungal infection, which comprises intravenously administering to a patient an effective amount of an injectable oil-in-water emulsion composition for intravenous administration comprising an oil component, an emulsifier and an antifungal triazole compound of the following formula (I)

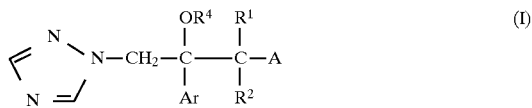

wherein Ar represents a substituted phenyl group; $R^1$ and $R^2$ represent, independently, a hydrogen atom or a lower alkyl group, or $R^1$ and $R^2$ may together form a lower alkylene group; $R^4$ represents a hydrogen atom or an acyl group; and A denotes an optionally substituted cyclic amide group bonded through a nitrogen atom, or a salt thereof, wherein said triazole compound is dissolved in said oil-in-water emulsion in a proportion of 0.0001 to 2% (W/V), wherein the oil component of said oil-in-water emulsion is a triglyceride of medium-size chain fatty acids having 6 to 14 carbon atoms, the amount of said oil component being 2 to 25% by weight, and wherein the emulsifier is lecithin, the amount of said emulsifier being 0.5 to 5% (W/V) and the proportion of said emulsifier relative to the total weight of the oil component being 1.0 to 15% by weight.

* * * * *